United States Patent

Astakhov et al.

Patent Number: 5,452,602
Date of Patent: Sep. 26, 1995

[54] PHOTOELECTRIC METHOD OF SEDIMENTATION ANALYSIS OF DISPERSION SYSTEMS OF HOMOGENEOUS SUBSTANCE

[75] Inventors: Alexandr V. Astakhov; Alexandr V. Bunin; Stanislav P. Khazov, all of Moscow, Russian Federation

[73] Assignee: Aktsionernoe Obschestvo "Agrokhim-Biznes", Moscow, Russian Federation

[21] Appl. No.: 211,477

[22] PCT Filed: Aug. 5, 1993

[86] PCT No.: PCT/RU93/00186

§ 371 Date: Apr. 5, 1994

§ 102(e) Date: Apr. 5, 1994

[87] PCT Pub. No.: WO94/03039

PCT Pub. Date: Feb. 17, 1994

[30] Foreign Application Priority Data

May 9, 1992 [RU] Russian Federation ............... 5057709

[51] Int. Cl.⁶ .......................... G01N 15/02; G01N 33/00
[52] U.S. Cl. .......................... 73/61.69; 73/61.65; 356/335; 356/336
[58] Field of Search ............... 73/61.69, 61.65; 356/335, 336, 337, 338

[56] References Cited

U.S. PATENT DOCUMENTS 3,676,647  7/1972  Staffin et al. .................. 235/92 PC
3,861,877  1/1975  Matharani et al. .............. 23/230 B (List continued on next page.)

FOREIGN PATENT DOCUMENTS 1598662  7/1973  Germany .
0260991  10/1988  Germany .................. 73/61.69

(List continued on next page.)

OTHER PUBLICATIONS

Kouzov, P. A. "Basics of Analysis. . ." Pub. Khimiya–Leningrad Division 1971 pp. 169–180.

Primary Examiner—Hezron E. Williams
Assistant Examiner—J. David Wiggins
Attorney, Agent, or Firm—Ladas & Parry

[57] ABSTRACT

A photoelectric method of sedimentation analysis of dispersion systems of a homogeneous substances, wherein a beam of rays having an arbitrary shape is first passed through an unloaded cell and the initial value of the photocurrent created by a non-scattered ray passing through the unloaded cell is measured. The length of the line h between two furtherest spaced from each other points of the projections of two light spots formed on the walls of an unloaded cell is determined on a plane parallel to the direction of sedimentation. Setting the value of the relative methodical error $\sigma$, the quantity H is determined. The beam of rays is positioned so that the middle of the line h is at a depth H from the surface of the suspension.

the cell is loaded with the suspension and the period of time $\tau$ is measured during which the optical density of the suspension of dispersed particles of powder remains constant from the moment sedimentation begins, and the relative optical density D(t) of the suspension is measured.

the radius $r_{max}$ of the largest powder particles is determined using Stoke's equation. And the velocity of the change of the relative optical density $\upsilon_D$ with $t > \tau$ is used to determine the density $v(r)$ of powder particle distribution as a function of radius, the density $\mu(r)$ of powder mass distribution, the mean value of the radius $<r>$, the mean square value of the radius $<r^2>$, and the standard deviation $\Delta$.

Scanning of the beam of rays is conducted to speed up sedimentation analysis, where for the beam of rays is positioned nearer to the bottom of the cell by a quantity $\Delta H$. A converging, diverging or parallel beam of rays is used, the rays being within the wavelength band of from $0.6 \mu$ to $0.05 \mu$.

20 Claims, 4 Drawing Sheets

U.S. PATENT DOCUMENTS

| | | | |
|---|---|---|---|
| 4,135,819 | 1/1979 | Schmid-Schönbein | 356/39 |
| 4,194,391 | 3/1980 | Rosenberger | 73/61.40 |
| 4,282,745 | 8/1981 | Burr | 73/61.40 |
| 4,514,257 | 4/1985 | Karlsson | 162/49 |
| 4,529,309 | 7/1985 | Pettersson | 356/335 |
| 4,696,571 | 9/1987 | Goldberg | 356/336 |
| 4,770,042 | 9/1988 | Cobb | 73/597 |
| 4,953,978 | 9/1990 | Bott | 356/336 |
| 5,257,087 | 10/1993 | Furuya | 356/336 |
| 5,309,216 | 5/1994 | Weichert | 356/335 |
| 5,316,729 | 5/1994 | Orth et al. | 422/73 |

FOREIGN PATENT DOCUMENTS

| | | | |
|---|---|---|---|
| 0807148 | 2/1981 | U.S.S.R. | 73/61.69 |
| 1490603 | 6/1989 | U.S.S.R. | 73/61.69 |
| 1635074 | 3/1991 | U.S.S.R. | |
| 1069680 | 8/1964 | United Kingdom . | |
| 1158338 | 7/1969 | United Kingdom . | |

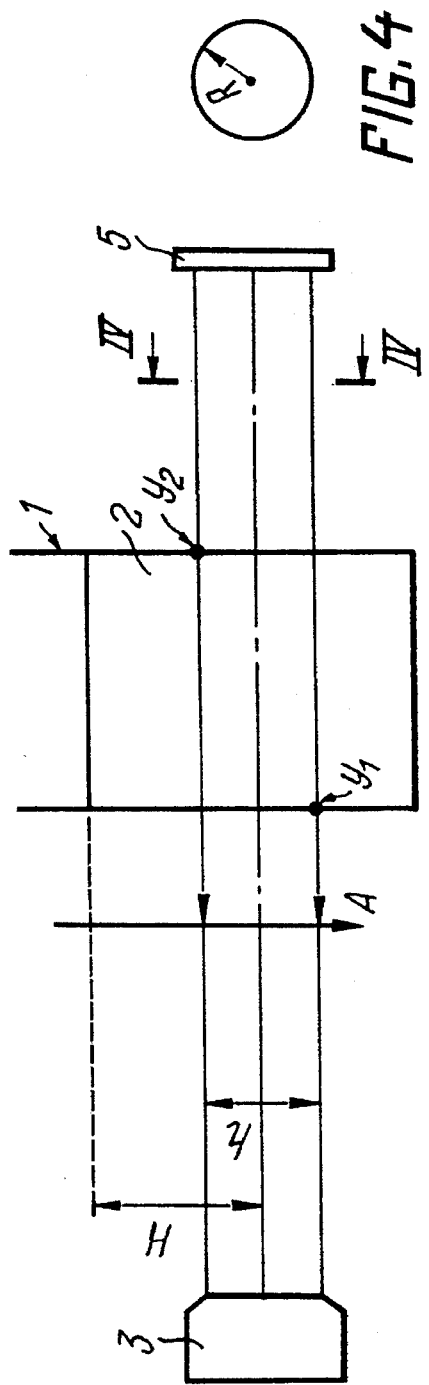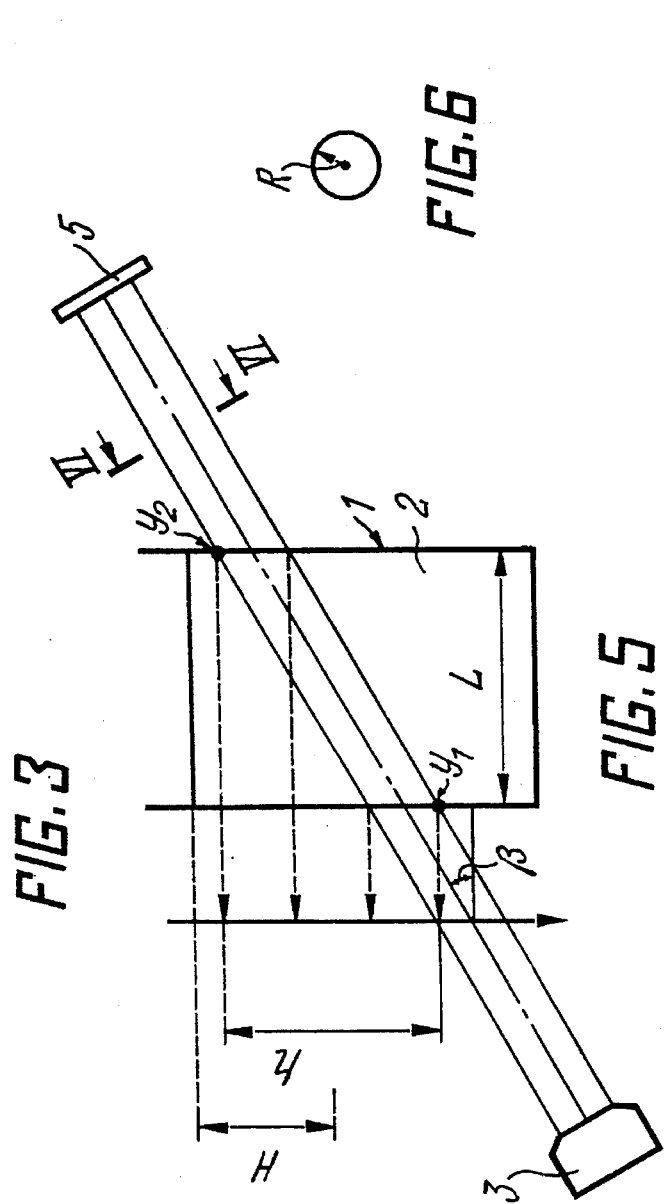

PHOTOELECTRIC METHOD OF SEDIMENTATION ANALYSIS OF DISPERSION SYSTEMS OF HOMOGENEOUS SUBSTANCE

FIELD OF INVENTION

The present invention relates to photoelectric methods of sedimentation analysis of the degree of dispersion of powder materials of a homogeneous substance. This method may be employed to measure the granular composition of powders in physical chemistry, instrumentation, pharmacology, the food industry in the manufacture of starch, flour, dried milk, chocolate, coffee, cacao, in the manufacture of mineral fertilizers and plant protection substances, synthetic materials, metallic powders, cement, ceramics, quartz, clay, etc.

BACKGROUND OF THE INVENTION

A method for measuring powder distribution on the basis of the granular composition of particles by photoelectric scanning and a device for the implementation of that method are known (see British Patent No. 1069680, Aug. 21, 1964) in which particle size distribution in a powder sample being analyzed is directly measured. This method is carried out in a scanning mode wherewith a narrow beam of light is moved in the direction of the force of gravity. In the case of a homogeneous suspension of particles, the particle size distribution curve may be obtained by measuring the relationship between particle concentration and depth. It is assumed that the lateral thickness of the light beam is negligibly small and the sedimentation of the suspension particles takes place in a stationary Stoke's mode. The method provides a calculation algorithm within the limits of these assumptions.

A narrow beam of light having a negligible cross-sectional thickness is used in the aforementioned method. However, the citerion defining fulfillment of this condition is not determined quantitatively, and therefore, there is no exact assessment of the measurement error due to the existence of a finite cross sectional area in real light beams.

In the mode of continuous scanning in the direction of the force of gravity there will always be a loss of information on the quantity of small-size particles ($r_{min}$), since they lag behind the scanning beam as they descent. Furthermore, measuring time increases when scanning is conducted in this direction.

In this method the moment at which sedimentation begins is taken as the starting point, following which after an arbitrary time period the source of light begins to move from the surface of the suspension downwards. Since the length of the pause after sedimentation begins is not fixed, the part of the powder consisting of larger particles with maximum radius is not fully registered.

A photoelectric method of sedimentation analysis of dispersion systems of a homogeneous substance is also known, wherein a beam of rays is passed through an unloaded cell and the initial value of the photocurrent created by a beam which is not scattered is measured. Then the cell is loaded with a suspension of uniformly dispersed particles of powder. The value of the photocurrent which is created by the non-scattered part of the beam is measured during the process of sedimentation. The relative optical density $D(t)$ of the suspension of dispersed particles of powder is measured according to the equation $$D(t) = \ln I_o/I_t$$

where $I_o$ is the photocurrent created by the beam of rays passing through the unloaded cell, $I_t$ is the photocurrent at the current moment of time t. Then, using Stoke's equation $\upsilon = \alpha r^2$, the values of the radii r of the particles descending in the suspension are determined, $\upsilon$ being the velocity of the descending particles (see, for example, P. A. Kouzov "Basics of Dispersion Analysis of Industrial Dust and Pulverized Materials," Leningrad, Khimaya, 1971, pp. 169–180).

Wherein, the relative optical density of the suspension is proportional to the total surface $S_o^r$ of particles of the dispersive phase, the radius of which is between zero and r $$S_o^r = K \ln I_o/I_t$$

where K is a constant characterizing the optical properties of the measuring system which do not depend on the process of sedimentation or on the properties of the photocurrent registering system, the surface $S_r^r$, of all particles whose radius is within the range of from r' to r is determined through $S_o^r$. Then, using the equation $$Q_{r1}^r = \frac{10^{-4}}{3} \rho F_m K S_{r1}^r = \frac{10^{-4}}{3} \rho r_m K \ln I_{r1}/I_r$$

the mass of the fractions whose particles have radii within the range of from r' to r is determined, $I_{r'}$ and $I_r$ being photocurrent values registered at the moments related to radii r' and r by Stoke's Law of sedimentation, $\rho$ is the density of particle material, $r_m$ is the mean arithmetic value of radii r' and r, the coefficient K is experimentally determined.

Furthermore, the aforementioned method provides for a beam of parallel light rays formed with a special "condenser-diaphragm" system being directed to the measuring cell in a direction perpendicular to its sides. The light scattered by the suspension passes through a second diaphragm, is focussed by means of a second condenser onto a photocell, and is converted into electric current which is registered by an instrument. It should be noted that the depth at which the beam passes relative to the suspension surface does not change in time.

Only the integral characteristics of dispersion are directly measured in the aforementioned method. Data of a differential character cannot be obtained without further processing. Both procedures require considerable time.

Systems forming collimated beams of parallel light rays, making the technical realization of the method more complicated, are used. The desired to create very narrow beams simultaneously makes the measurement results sensitive to fluctuations in the suspension, which distort Stoke's model of gravitational sedimentation.

Serious problems arise when consideration is given to the use of the method with particles which approach Brownian motion behavior by size and character of movement. The reason is that there is no quantitative assessment of the effect of movement of particles of this type on measurement error.

DISCLOSURE OF THE INVENTION

At the base of the present invention lies the task of creating a photoelectric method of sedimentation analysis of dispersion systems of a homogeneous substance, which would make it possible, taking into account the geometrical parameters of the radiated beam, to determine the quantity of particles of each fraction of a dispersion system in a shorter analyzing time, and at the same time enhance the metrological accuracy of measurement.

This task is resolved in a photoelectric method of sedimentation analysis of dispersion systems of a homogeneous substances, wherein a beam is passed through an unloaded cell and the initial value of photocurrent, created by non-scattered light that has passed through the unloaded cell, is measured, the cell is loaded with a suspension in which the powder particles are uniformly dispersed, the value of the photocurrent created by the non-scattered part of the light that has passed through the cell is measured in the process of sedimentation, the optical density D(t) of the suspension of dispersed powder particles is calculated, using the equation $$D(t) = \ln I_o/I_t$$

where $I_o$ is the value of the photocurrent created by non-scattered light that has passed through the unloaded cell, $I_t$ is the value of photocurrent created by the non-scattered part of light at a current moment t and, using Stoke's equation, $$\upsilon = \alpha r^2,$$

the radii r of the particles that are descending in the suspension are determined, where $\upsilon$ is the velocity of sedimentation and $\alpha$ is a proportionality coefficient, determined by the equation $$\alpha\alpha = \frac{2(\rho_m - \rho_g)g}{g\eta}$$

where $\rho_m$ is the density of the powder particles, $\rho_g$ is the density of the liquid phase at the measurement temperature, g is the acceleration of gravity, $\eta$ is the dynamic viscosity of the liquid phase at the measurement temperature, in that according to the invention, a beam of rays from a radiation source is used, the beam having an arbitrary cross-sectional shape, the projection length h of the line between the two furtherest spaced from each other points of two light spots which are created by the non-scattered beam of rays on the walls of an unloaded cell on an axis parallel to the direction of sedimentation, is determined for each beam shape used, the value of the relative methodical error $\sigma$ is preset using the equation $$\sigma = .5 \, (h/2H)^2$$

to a value within the range of from 0.1% to 0.00001%, this being used to determine this value of H, using the equation $$H = .35 \, h/\sigma^{1/2}$$

the beam of rays is disposed so that the middle of the line h is at a depth H from the surface of the suspension, the time interval $\tau$ during which the optical density of the suspension of dispersed particles remains constant from the moment sedimentation begins is measured, and the relative optical density of the suspension $D(\tau)$ during that time interval $\tau$ is measured using the equation $$D(\tau) = \ln I_o I_t,$$

the maximum radius $r_{max}$ of the largest particles of the powder is determined taking this time interval into account and using Stoke's equation $$r_{max} = \sqrt{\frac{H}{\alpha\tau}}$$

the velocity $\upsilon_D$ at which the relative optical density changes with t<$\tau$ is determined, using the equation $$\upsilon_D = \frac{dD(t)}{dt}$$

and the density $\nu$ (r) of powder particle distribution is determined as a function of the radius, using the equation $$\upsilon(r) = \frac{2}{r_{max}} \cdot \frac{t^{5/2}\upsilon_p(t)|_t = H/\alpha r^2}{\tau^{3/2}D(\tau) + \tau^{1/2}\int_\tau^\infty \alpha t D(t)}$$

When carrying out the sedimentation analysis of dispersion systems, it is advisable that scanning of the beam of rays be effected. Accordingly, the beam of rays is positioned so that the middle of the line h is at a depth of (H+$\Delta$H) from the surface of the suspension, wherein $$(H+\Delta H) < H_{max},$$

where $H_{max}$ is the distance from the surface of the suspension to the bottom of the cell, after the cell is loaded with a suspension of uniformly dispersed powder particles, the beam of rays is displaced in the direction opposite to the direction of sedimentation at a constant velocity U, which can be determined by the inequality $$U < \alpha \, r_{max}^2 \frac{\Delta H}{H},$$

the time interval $\tau_1$ during which the optical density of the suspension of dispersed particles remains constant from the moment the scanning begin is measured, and the radius of the largest powder particles is determined using Stoke's equation and taking the time interval $\tau_1$ into account, $$r_{max} = \sqrt{\frac{H + \Delta H - U\tau_1}{\alpha\tau_1}}$$

the scanning time T=$\Delta$H/U is determined, and the density $\nu$(r) of the powder particle distribution as a function of radius is determined using the equation $$\upsilon(r) = -\frac{2}{r_{max}} - \frac{A_1(t) \, t^{5/2} \cdot \upsilon_D(t) \, |_t = H(t)/\alpha r^2}{\tau_1^{3/2}D(\tau_1) + \tau_1^{1/2}\int_{\tau_1}^\infty dt B_1(t)D(t)}$$

where $$A_j(t) =$$

$$B_I(t) = \begin{cases} \dfrac{(H+\Delta H - U\tau_1)^{3/2}}{(H+\Delta H)(H+\Delta H - Ut)^{1/2}} & \text{with } \tau_1 \leq t \leq T \\ \dfrac{(H+\Delta H - U\tau_1)^{3/2}}{(H+\Delta H - UT)^{3/2}} & \text{with } t > T \end{cases}$$

$$B_I(t) = \begin{cases} \dfrac{(H+\Delta H)(H+\Delta H - U\tau_1)}{(H+\Delta H - Ut)^2} & \text{with } \tau_1 \leq t \leq T \\ \dfrac{H+\Delta H - U\tau_1}{H+\Delta H - UT} & \text{with } t > T \end{cases}$$

and the scanning is terminated when the beam reaches the depth H.

When a sedimentation analysis of dispersion systems is being conducted, it is useful to effect the scanning of the beam of rays. Accordingly, the beam of rays is so positioned that the middle of the line h is at a depth $(H+\Delta H)$ from the surface of the suspension, wherein $(H+\Delta H) < H_{max}$, where $H_{max}$ is the distance from the surface of the suspension to the bottom of the cell, after the cell has been loaded with a suspension of uniformly dispersed powder particles, the time interval $\tau_2$, during which the optical density of the suspension of dispersed particles of powder remains constant from the moment sedimentation began is measured prior to the scanning, and taking this time interval $\tau_2$ into account, the radius $r_{max}$ of the largest particles of powder is determined using Stoke's equation in accordance with the equation $$r_{max} = \sqrt{\dfrac{H+\Delta H}{\alpha \tau_2}}$$

from the moment $\tau_2$ the beam of rays is displaced in the direction opposite to the direction of sedimentation at a constant velocity U, determined by the inequality $$U < \alpha r_{max}^2 \dfrac{\Delta H}{H}.$$

the scanning time $T = \Delta H / U$ is determined, and the density $\upsilon(r)$ of the powder particle distribution as a function of radius is determined using the equation $$\upsilon(r) = -\dfrac{2}{r_{max}} \cdot \dfrac{A_1(t) \, t^{5/2} \cdot \upsilon_D(t)|_{t = H(t)/\alpha r^2}}{\tau_2 D(\tau_2) + \tau_2^{1/2} \displaystyle\int_{\tau_2}^{\infty} dt B_1(t) D(t)}$$

where $$A_I(t) = \begin{cases} \dfrac{(H+\Delta H - U\tau_2)^{3/2}}{(H+\Delta H)(H+\Delta H - Ut)^{1/2}} & \text{with } \tau_2 \leq t \leq T \\ \dfrac{(H+\Delta H - U\tau_2)^{3/2}}{(H+\Delta H - UT)^{3/2}} & \text{with } t > T \end{cases}$$

$$B_I(t) = \begin{cases} \dfrac{(H+\Delta H)(H+\Delta H - U\tau_2)}{(H+\Delta H - Ut)^2} & \text{with } \tau_2 \leq t \leq T \\ \dfrac{H+\Delta H - U\tau_2}{H+\Delta H - UT} & \text{with } t > T \end{cases}$$

and the scanning is terminated when the beam reaches the depth H.

The set task is also resolved in a photoelectric method of sedimentation analysis of dispersion systems of a homogeneous substance, wherein the beam is passed through an unloaded cell and the initial value of the photocurrent created by a non-scattered beam that has passed through the unloaded cell is measured, the cell is loaded with a suspension of uniformly dispersed powder particles, in the process of sedimentation the value of the photocurrent created by the non-scattered part of the beam that has passed through the cell is measured, and the relative optical density D(t) of the suspension of the dispersed powder particles is measured using the equation $$D(t) = \ln I_o/I_t,$$

where $I_o$ is the value of the photocurrent created by the non-scattered beam that has passed through the unloaded cell, $I_t$ is the value of the photocurrent created by the non-scattered part of the beam that has passed through the cell at a current moment of the time t and, using Stoke's equation, $$\upsilon = \alpha r^2,$$

the values of the radii r of the particles that are descending in the suspension are determined, where $\upsilon$ is the velocity of particle sedimentation and $\alpha$ is the proportionality coefficient determined by the equation $$\alpha = \dfrac{2(\rho_m - \rho_g)g}{g\eta}.$$

where $\rho_m$ is the powder particle density, $\rho_g$ is the density of the liquid phase of the suspension, $\eta$ is the dynamic viscosity of the liquid phase at the measurement temperature, and g is the acceleration of gravity, in that according to the invention a beam of rays from a radiation source is used, the beam having an arbitrary cross-sectional shape, the projection length h of the line between two furtherest spaced from each other points of two light spots, which are created by the non-scattered beam of rays on the walls of an unloaded cell on an axis parallel to the direction of sedimentation, is determined for each beam shape used, the value of the relative methodical error $\sigma$ is preset using the equation $$\sigma = .5 \, (h/2H)^2$$

to a value within the range of from 0.1% to 0.00001%, this being used to determine the value of H, using the equation $$H = .35 \, h/\sigma^{1/2}$$

the beam of rays is disposed so that the middle of the line h is at a depth H from the surface of the suspension, the time interval $\tau$ during which the optical density of the suspension of dispersed powder particles remains constant from the moment when sedimentation begins is measured, and the relative optical density of the suspension D(96) during that time interval τ is measured using the equation $$D(\tau) = \ln I_o/I_t,$$

the radius $r_{max}$ of the largest powder particles is determined taking this time interval into account and using Stoke's equation, $$r_{max} = \sqrt{\frac{H}{\alpha\tau}},$$

the velocity of changes in the relative optical density $v_D$ with t>τ is determined using the equation $$v_D = \frac{dD(t)}{dt},$$

and the density ν(r) of the powder mass distribution is determined according to the values of radii of the powder particles, using the equation $$\mu(r) = -\frac{2}{r_{max}} \cdot \frac{t \cdot v_D(t) \, |t = H|\alpha r^2}{D(\tau) - \frac{1}{2}\tau^{1/2} \int_\tau^\infty \frac{dt}{t^{3/2}} D(t)}.$$

When the sedimentation analysis of dispersion systems is being carried out it is advisable that scanning of the beam of rays be effected. Accordingly, the beam of rays is positioned so that the middle of the line h is at a depth of (H+ΔH) from the surface of the suspension, wherein $$(H+\Delta H) < H_{max},$$

where $H_{max}$ is the distance from the surface of the suspension to the bottom of the cell, after the cell is loaded with a suspension of uniformly dispersed powder particles the beam is displaced in the direction opposite to the direction of sedimentation at a constant velocity U which is determined by the inequality $$U < \alpha r_{max}^2 \frac{\Delta H}{H},$$

the time interval $\tau_1$ during which the optical density of the suspension of dispersed powder particles remains constant from the moment the scanning began is measured, and the radius of the largest powder particles is determined, using Stoke's equation and taking the time interval $\tau_1$ into account, by $$r_{max} = \sqrt{\frac{H + \Delta H - U\tau_1}{\alpha\tau_1}},$$

the scanning time T=ΔH/U is determined, and the density μ(r) of the distribution of the powder mass as a function of radius is determined using the equation $$\mu(r) = -\frac{2}{r_{max}} \cdot$$

-continued $$\frac{A_2(t) \, v_D(t) \, |t = H(t)|\alpha \cdot r^2}{D(\tau_1) + C(\tau_1, T)D(T) - \frac{1}{2}\tau_1^{1/2} \int_{\tau_1}^\infty \frac{dt}{t^{3/2}} B_2(t)D(t)}$$

where $$A_2(t) = \begin{cases} \frac{H + \Delta H - Ut}{H + \Delta H} & \text{with } \tau_1 \leq t \leq T \\ 1 & \text{with } t > T, \end{cases}$$

$$C(\tau_1, T) = \left(\frac{\tau_1}{T}\right)^{1/2} \cdot \left[\frac{(H + \Delta H - UT)^2}{(H + \Delta H - U\tau_1)^2} - \frac{(H + \Delta H - UT)^{1/2}}{(H + \Delta H - U\tau_1)^{1/2}}\right]$$

$$B_2(t) = \begin{cases} \frac{H + \Delta H}{(H + \Delta H - Ut)^{1/2}(H + \Delta H - U\tau_1)^{1/2}} & \text{with } t \leq T \\ \frac{(H + \Delta H - UT)^{1/2}}{(H + \Delta H - U\tau_1)^{1/2}} & \text{with } t \geq T \end{cases}$$

and the scanning is terminated when the beam reaches the depth H.

When a sedimentation analysis of dispersion systems is being conducted, it is useful to effect scanning of the beam of rays. Accordingly, the beam is so positioned that the middle of the line is at a depth (H+ΔH) from the surface of the suspension, wherein $$(H+\Delta H) < H_{max},$$

where $H_{max}$ is the distance from the surface of the suspension to the bottom of the cell, after the cell has been loaded with a suspension of powder particles uniformly dispersed in a liquid, the interval of time $\tau_2$ during which the optical density of the suspension of dispersed powder particles remains constant from the moment the sedimentation begins is measured prior to the scanning, and using Stoke's equation and taking this time interval $\tau_2$ into account, the radius $r_{max}$ of the largest powder particles is determined in accordance with equation $$r_{max} = \sqrt{\frac{H + \Delta H}{\alpha\tau_2}},$$

displacement of the beam of rays is conducted from the moment of time $\tau_2$ in the direction opposite to the direction of sedimentation at a constant velocity U, determined by the inequality $$U < \alpha r_{max}^2 \frac{\Delta H}{H},$$

the scanning time $$T = \Delta H/U$$

is determined, and the density ν(r) of the distribution of powder mass is determined according to the values of the radii of powder particles where $$A_2(t) = \begin{cases} \dfrac{H+\Delta H - Ut}{H+\Delta H} & \text{with } \tau_2 \leq t \leq T \\ 1 & \text{with } t > T \end{cases}$$

$$C(\tau_2, T) =$$

$$\left(\dfrac{\tau_2}{T}\right)^{1/2} \cdot \left[ \dfrac{(H+\Delta H - UT)^2}{(H+\Delta H - U\tau_2)^2} - \dfrac{(H+\Delta H - UT)^{1/2}}{(H+\Delta H - U\tau_2)^{1/2}} \right]$$

$$B_2(t) = \begin{cases} \dfrac{H+\Delta H}{(H+\Delta H - Ut)^{1/2}(H+\Delta H - U\tau_2)^{1/2}} & \text{with } t \leq T \\ \dfrac{(H+\Delta H - UT)^{1/2}}{(H+\Delta H - U\tau_2)^{1/2}} & \text{with } t \geq T \end{cases}$$

and the scanning is terminated when the beam reaches depth H.

The set task is also resolved in a photoelectric method of sedimentation analysis of dispersion systems of a homogeneous substance, wherein the beam is passed through an unloaded cell and the initial value of the photocurrent created by the non-scattered beam that has passed through the unloaded cell is measured, the cell is loaded with a suspension of powder particles uniformly dispersed in a liquid, during sedimentation the photocurrent which is created by the non-scattered part of the beam that has passed through the cell is measured, and the relative optical density $D(t)$ of the suspension of dispersed powder particles is measured, using the equation $$D(t) = \ln I_o / I_t,$$

where $I_o$ is the value of the photocurrent created by the non-scattered beam that has passed through the unloaded cell, $I_t$ is the value of the photocurrent created by the non-scattered part of the beam that has passed through the cell at a current moment of time t, and using Stoke's equation, $$\upsilon = \alpha r^2,$$

the value of the radii r of the particles that are descending in the suspension are determined, where $\upsilon$ is the velocity of particle sedimentation and $\alpha$ is the proportionality coefficient, determined by the equation $$\alpha = \dfrac{2(\rho_m - \rho_g)g}{g \eta}$$

where $\rho_m$ is the powder particle density, $\rho_g$ is the density of the liquid phase of the suspension, $\eta$ is the dynamic viscosity of the liquid phase at the measurement temperature, g is the acceleration of gravity, in that according to the present invention a beam of rays from a source of radiation is used, the beam having an arbitrary cross-sectional shape, and the projection length h of the line between the two furtherest spaced from each other points of two light spots, which are created by the non-scattered beam of rays on the walls of the unloaded cell, on the axis parallel to the direction of sedimentation, is determined for each beam shape used, and the value of relative methodical error $\sigma$ is preset using the equation $$\sigma = .5 \, (h/2H)^2$$

to within the range of 0.1% to 0.0001%, this being used to determine the value of H, using the equation $$H = .35 \, h/\sigma^{1/2}$$

the beam of rays is disposed so that the middle of the line h is at the depth H from the surface of the suspension, the interval of time $\tau$ during which the optical density of the suspension of disposed powder particles remains constant from the moment at which sedimentation begins is measured, and the relative optical density of the suspension $D(\tau)$ in that time interval is measured according to the equation $$D(\tau) = \ln I_o / I_\tau$$

using the Stoke's equation and taking into account that interval of time the radius of the largest particles of powder is determined by the equation $$r_{max} = \sqrt{\dfrac{H}{\alpha \tau}} \, ,$$

the velocity of change of the relative optical density $\upsilon_D$ with $t > \tau$ is determined using the equation $$\upsilon_D = \dfrac{dD(t)}{dt} \, ,$$

and the integral characteristics of the degree of dispersion of the powder particles are determined: the mean value of the radius $<r>$ of powder particles by the equation $$<r> = r_{max} \dfrac{1 + \dfrac{1}{2\tau^{1/2} D(\tau)} \int_\tau^\infty \dfrac{dt}{t^{1/2}} D(t)}{1 + \dfrac{1}{\tau D(\tau)} \int_\tau^\infty dt D(t)}$$

the mean square value of the radius $<r^2>$ of the powder particles by the equation $$<r^2> = \dfrac{r_{max}^2}{1 + \dfrac{1}{\tau D(\tau)} \int_\tau^\infty dt D(t)}$$

and the standard deviation $\Delta$ between the radius and the squared radius by the equation $$\Delta = \dfrac{(<r^2> - <r>^2)^{1/2}}{<r>}$$

When the sedimentation analysis of dispersion systems is being carried out it is advisable that scanning of the beam of rays be effected. Accordingly, the beam of rays is positioned so that the middle of the line h is at a depth of $(H+\Delta H)$ from the surface of the suspension, wherein $$(H+\Delta H) < H_{max},$$

where $H_{max}$ is the distance from the surface of the suspension to the bottom of the cell, after the cell is loaded with a suspension of uniformly dispersed powder particles, the beam is displaced in the direction opposite to the direction of sedimentation at a constant velocity U which is determined by the inequality $$U < \alpha \, r_{max}^2 \frac{\Delta H}{H},$$

the time interval $\tau_1$ during which the optical density of the suspension of dispersed powder particles remains constant from the moment the scanning begins is measured, and the radius of the largest powder particles is determined, using Stoke's equation and taking the time interval $\tau_1$ into account $$r_{max} = \sqrt{\frac{H + \Delta H - U\tau_1}{\alpha \, \tau_1}},$$

the scanning time $T = \Delta H/U$ is determined, and the integral characteristics of the degree of dispersion of the powder particles are determined: the mean value of the radius $\langle r \rangle$ of powder particles by the equation $$\langle r \rangle = r_{max} \frac{1 + \frac{1}{2\tau_1^{1/2} D(\tau_1)} \int_{\tau_1}^{\infty} \frac{dt}{t^{1/2}} B_3(t) D(t)}{1 + \frac{1}{\tau_1 D(\tau_1)} \int_{\tau_1}^{\infty} dt B_1(t) D(t)},$$

where $B_1$ is as defined above, $$B_3(t) = \begin{cases} \dfrac{H + \Delta H}{H + \Delta H - Ut} & \text{with } t \leq T \\[2mm] \dfrac{(H + \Delta H - U\tau_1)^{1/2}}{(H + \Delta H - UT)^{1/2}} & \text{with } t \geq T \end{cases}$$

the mean square value of the radius of the particles $\langle r^2 \rangle$ of the powder particles by the equation $$\langle r^2 \rangle = \frac{r_{max}^2}{1 + \frac{1}{\tau_1 D(\tau_1)} \int_{\tau_1}^{\infty} dt B_1(t) D(t)}$$

and the standard deviation $\Delta$ between the radius and the squared radius $$\Delta = \frac{(\langle r^2 \rangle - \langle r \rangle^2)^{1/2}}{\langle r \rangle}$$

and the scanning is terminated when the beam reaches the depth H.

When a sedimentation analysis of dispersion systems is being carried out, it is useful to effect scanning of the beam of rays. Accordingly, the beam of rays is so positioned that the middle of the line is at a depth $(H+\Delta H)$ from the surface of the suspension, wherein $$(H+\Delta H) < H_{max},$$

where $H_{max}$ is the distance from the surface of the suspension to the bottom of the cell, after the cell has been loaded with a suspension of powder particles uniformly dispersed in a liquid, the interval of time $\tau_2$ during which the optical density of the suspension of dispersed powder particles remains constant from the moment sedimentation begins is measured prior to the scanning, and according to Stoke's equation, taking that interval of time $\tau_2$ into account, the radius $r_{max}$ of the largest powder particles is determined in accordance with the equation $$r_{max} = \sqrt{\frac{H + \Delta H}{\alpha \, \tau_2}},$$

the beam of rays is displaced from the moment of time $\tau_2$ in the direction opposite to the direction of sedimentation at a constant velocity U, determined by the inequality $$U < \alpha \, r_{max}^2 \frac{\Delta H}{H},$$

the scanning time $T = \Delta H/U$ is determined and the integral characteristics of the degree of dispersion of the powder particles are determined: the mean value of the radius $\langle r \rangle$ of powder particles by the equation $$\langle r \rangle = r_{max} \frac{1 + \frac{1}{2\tau_2^{1/2} D(\tau_2)} \int_{\tau_2}^{\infty} \frac{dt}{t^{1/2}} B_3(t) D(t)}{1 + \frac{1}{\tau_2 D(\tau_2)} \int_{\tau_2}^{\infty} dt B_1(t) D(t)},$$

where $B_1$ is as defined above, $$B_3(t) = \begin{cases} \dfrac{H + \Delta H}{H + \Delta H - Ut} & t \leq T \\[2mm] \dfrac{(H + \Delta H - U\tau_2)^{1/2}}{(H + \Delta H - UT)^{1/2}} & t \geq T \end{cases}$$

the mean square value of the radius $\langle r^2 \rangle$ of the powder particles by the equation $$\langle r^2 \rangle = \frac{r_{max}^2}{1 + \frac{1}{\tau_2 D(\tau_2)} \int_{\tau_2}^{\infty} dt B_1(t) D(t)}$$

and the standard deviation $\Delta$ between the radius and the squared radius $$\Delta = \frac{(\langle r^2 \rangle - \langle r \rangle^2)^{1/2}}{\langle r \rangle},$$

and the scanning is terminated when the beam reaches the depth H.

It is advantageous that the suspension of powder particles uniformly dispersed in a liquid be heated to a temperature of $T°K$, at which the Brownian motion of the smallest particles having a radius of from 5 μ to 0.01 μ can be neglected and the distance H from the surface of the suspension to the middle of the line h be increased proportionally so that the condition $$\frac{0.12 \cdot K}{\sigma(\rho_m - \rho_g) g \, r_{min}^3} \left( \frac{T}{H} \right) \ll 1$$

is maintained.

It is advantageous that a beam of cylindrical shape with a radius R of the cross section be used, the axis of which is perpendicular to the direction of sedimentation and is positioned at the depth H.

It is advisable that a beam of cylindrical shape with a radius R of the cross section be used, the axis of which is positioned at an incident angle $\beta$ to the direction of sedimentation and is determined from the condition $$L\, tg\, \beta + \frac{2R}{\cos\gamma} \leq 2.83\, H\, \sigma^{1/2},$$

where L is the distance between the walls of the cell.

It is advantageous that a converging beam of rays be used, the axis of which is perpendicular to the direction of sedimentation, and the convergence angle $\gamma$ is determined from the condition $$2(L+L_o)\, tg\, \frac{\gamma}{2} \leq 2.83\, H\, \sigma^{1/2},$$

where $L_o$ is the distance from the cone apex to the nearest wall along a normal thereto.

It is advantageous that a converging beam of rays be used, the axis of which is positioned at an incident angle $\beta$ to the direction of sedimentation and the convergence angle $\gamma$ is determined from the equation $$L_1 \sin\left(\beta + \frac{\gamma}{2}\right) - L_2 \sin\left(\beta - \frac{\gamma}{2}\right) \leq 2.83\, H\, \sigma^{1/2}$$

where $L_1$ is the maximum distance from the cone apex to the intersection of the beam of rays with the far wall of the cell, $L_2$ is the minimum distance from the cone apex to the intersection of the beam of rays with the near wall of the cell.

It is advisable to use a diverging beam of rays, the axis of which is perpendicular to the direction of sedimentation, and the divergence angle $\theta$ is determined from the condition $$2(L+L_3)\, tg\, \frac{\theta}{2} \leq 2.83\, H\, \sigma^{1/2},$$

where $L_3$ is the distance from the source of radiation to the near wall of the cell along a normal thereto.

It is advantageous to use a diverging beam of rays, the axis of which is positioned at an incident angle $\beta$ to the direction of sedimentation and the divergence angle $\theta$ is determined from the condition $$L_4 \sin\left(\beta + \frac{\theta}{2}\right) - L_5 \sin\left(\beta - \frac{\theta}{2}\right) \leq 2.83\, H\, \sigma^{1/2}$$

where $L_4$ is the maximum distance from the source to the intersection of the beam of rays with the far wall of the cell, $L_5$ is the minimum distance from the source to the intersection of the beam with the near wall of the cell.

It is also advisable that rays be used which are within the wavelength band from 0.6 $\mu$ to 0.05 $\mu$.

The principal advantage of the claimed method is that the differential distribution of the particles in the powder sample being analyzed and the mass thereof are directly determined according to the size of the particles, excluding two traditional intermediate stages: the direct determination of the integral characteristics and the subsequent differential analysis. The required measuring time is minimal, it is 2–50 times less than that required in known methods.

In the claimed method strict requirements are not imposed on the shape of the beam of light used, on the size of the cross section, or on the angle at which the beam of light is directed relative to the direction of sedimentation. These distinctive features make it possible in one measuring cycle to substantially reduce the influence of various fluctuations in the suspension on the accuracy of the measurement and to expand the range of particles being measured due to spatial averaging of the scattering effects, since a sufficiently large volume of the suspension is irradiated. A simple device can be used to realize the method, since there is no necessity for collimated beams of light which are of negligibly small size in their cross section or for additional alignment of the beam with respect to the side walls of the measuring cell.

The claimed method is based on a principle which is completely different from those known in that it is based on the dependence of the analyzing time on the required measurement accuracy, attained by corresponding selection of the optimum depth at which the beam of light is positioned relative to the surface of the suspension in the measuring cell. Thus a quantitative assessment of the error and measuring time is obtained.

One of the principle distinguishing features of the proposed method is the substantial, by more than two times, reduction of measuring time for particles approaching Brownian in respect of size and character of movement, i.e. in the range from 5 to 0.01 $\mu$, attained by increasing the temperature of the suspension, taking into account the required measurement accuracy.

BRIEF DESCRIPTION OF DRAWINGS

Further on the invention is explained by concrete embodiments with reference to the accompanying drawings, wherein:

FIG. 3 is a schematic view of a cell and a beam of rays of cylindrical shape, the axis of which is perpendicular to the direction of sedimentation, according to the present invention;

FIG. 4 is a section along line IV—IV in FIG. 3, according to the invention;

FIG. 5 is a schematic view of a cell and beam of rays, the axis of which is positioned at an incident angle $\beta$ to the direction of sedimentation, according to the invention;

FIG. 6 is a section along line VI—VI in FIG. 5, according to the present invention;

EMBODIMENTS OF THE INVENTION

Figure 1:
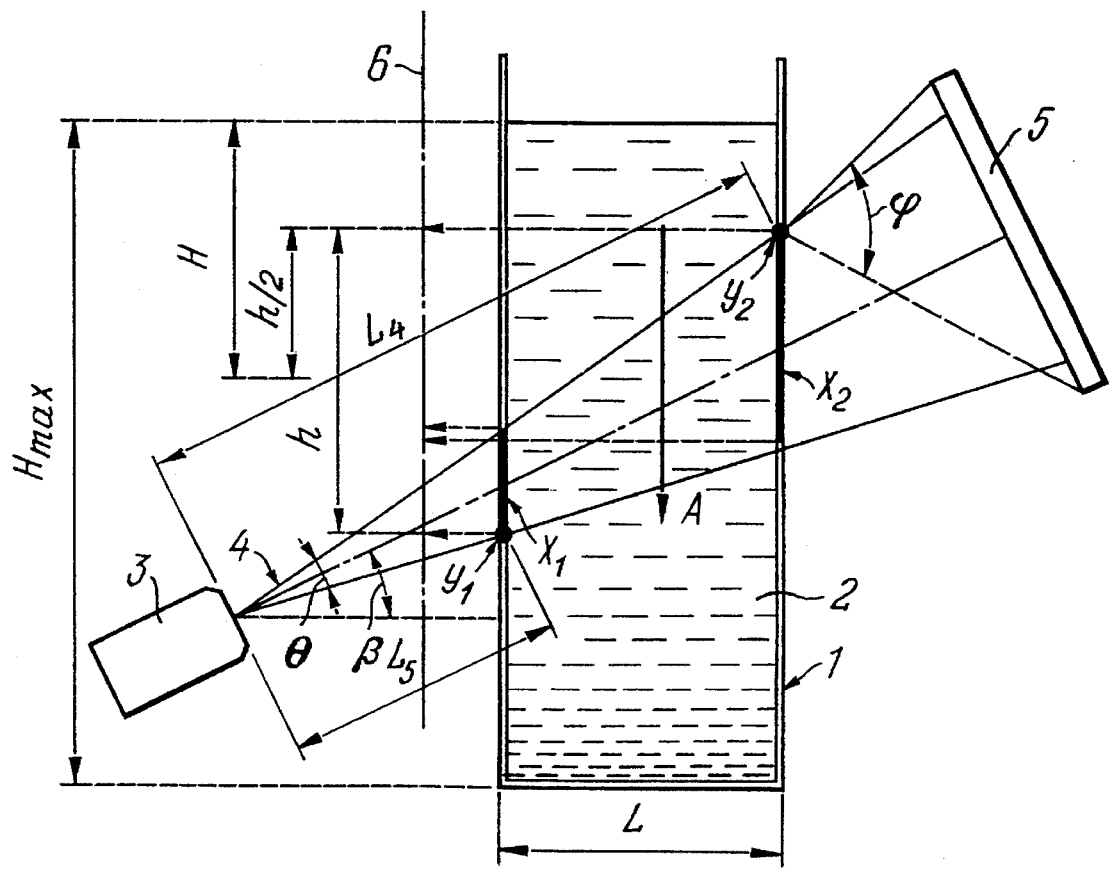
FIG. 1 is a schematic view of a device for realization of a photoelectric method of sedimentation analysis of dispersion systems of a homogeneous substance, according to the present invention.

A device comprising a cell 1 (FIG. 1), inside which a suspension 2 to be analyzed is disposed, is used to implement the proposed method of sedimentation analysis of dispersion systems of a homogeneous substance.

A source 3 of radiation is positioned on one side of the cell 1. The beam 4 of rays from the source is directed to the cell 1.

A photocell 5 is positioned on the other side of the cell 1, the purpose of the photocell being to receive rays passing through the cell 1.

Figure 2:
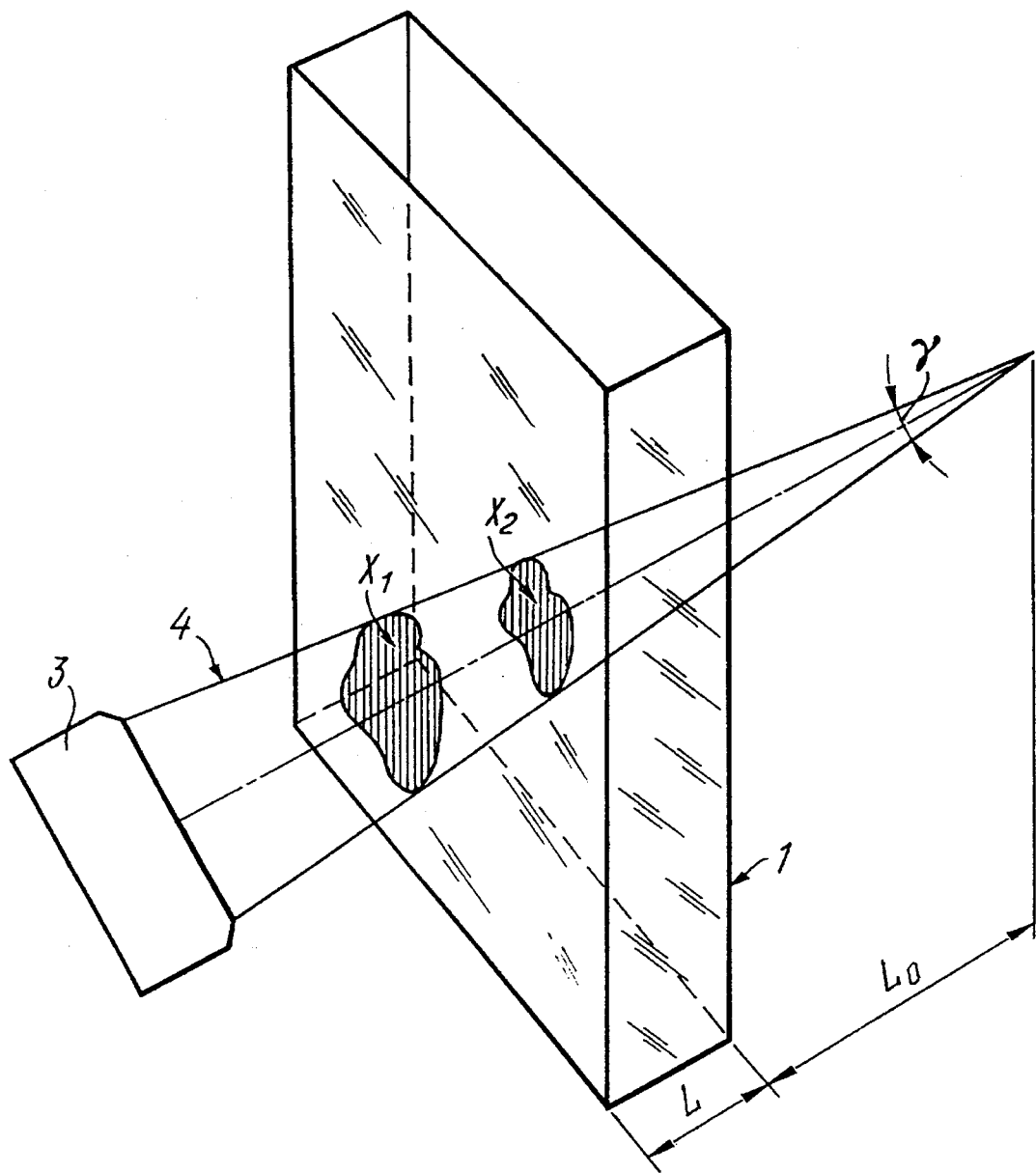
FIG. 2 is a general view in perspective of a cell and two light spots created by a beam of rays on the cell's walls, according to the invention.

A beam 4 (FIG. 2) of rays of arbitrary shape passing through an unloaded cell 1 creates two light spots X1 and X2 on the walls of cell 1.

If the rays are of arbitrary shape then the light spots X1 and X2 on the walls of cell 1 are also of arbitrary shape.

The length h (FIG. 1) of the projection of the line between the two furtherest spaced from each other points $y_1$ and $y_2$ of the two light spots X1 and X2 is determined for each shape of beam used. The spots are created by the non-scattered beam 4 on the walls of the unloaded cell 1 on an axis 6 parallel to the direction of sedimentation designated by arrow A.

The distance H is the depth at which the middle of the projection of line h lies below the surface of the suspension.

Usually a beam of rays of cylindrical shape (FIG. 3) having a radius R of a cross section h=2R (FIG. 4) is used to realize the said method, the axis of the beam being perpendicular to the direction of sedimentation and positioned at a depth H from the surface of the suspension.

An embodiment is possible when a beam of rays of cylindrical shape with a radius R of the cross section is used, the axis of the beam being positioned at an incident angle β (FIG. 5) to the direction of sedimentation and is determined by the condition $$Ltg\beta + \frac{2R}{\cos\beta} \leq 2.83 H\sigma^{1/2},$$

where L is the distance between the walls of the cell.

An embodiment is also possible when a converging beam 4 of rays (FIG. 2) is used, the axis of which is perpendicular to the direction of sedimentation and the convergence angle Θ is determined from the condition $$2(L+L_o)tg\frac{\gamma}{2} \leq 2.83 H\sigma^{1/2},$$

where $L_o$ is the distance from the cone apex to the near wall of cell 1 along a normal thereto.

Figure 7:
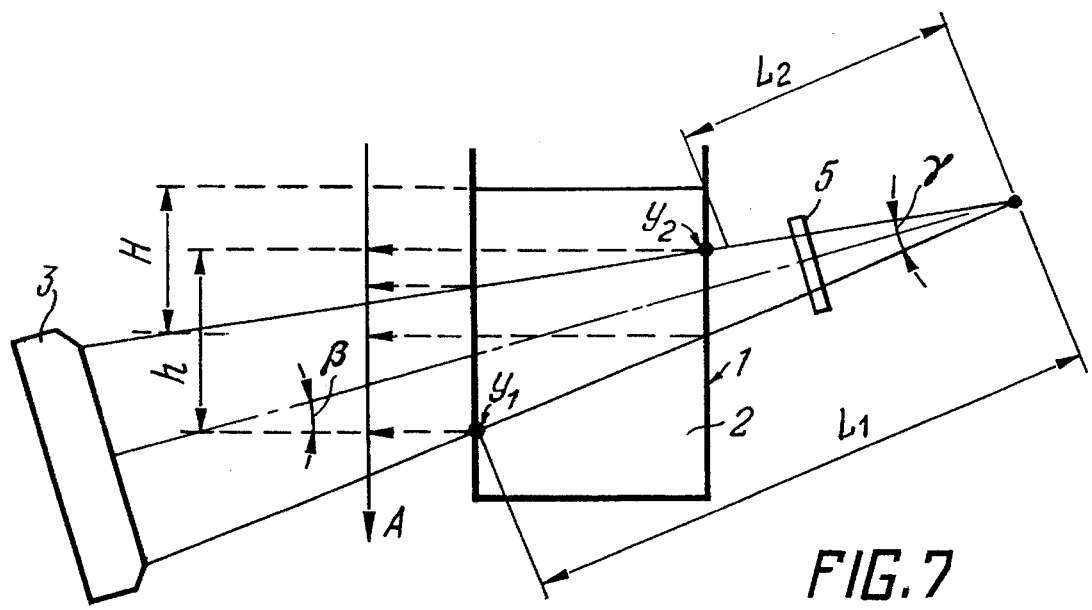
FIG. 7 is a schematic view of a cell and beam of converging rays, the axis of which is positioned at an incident angle $\beta$ to the direction of sedimentation, according to the present invention.
Figure 8:
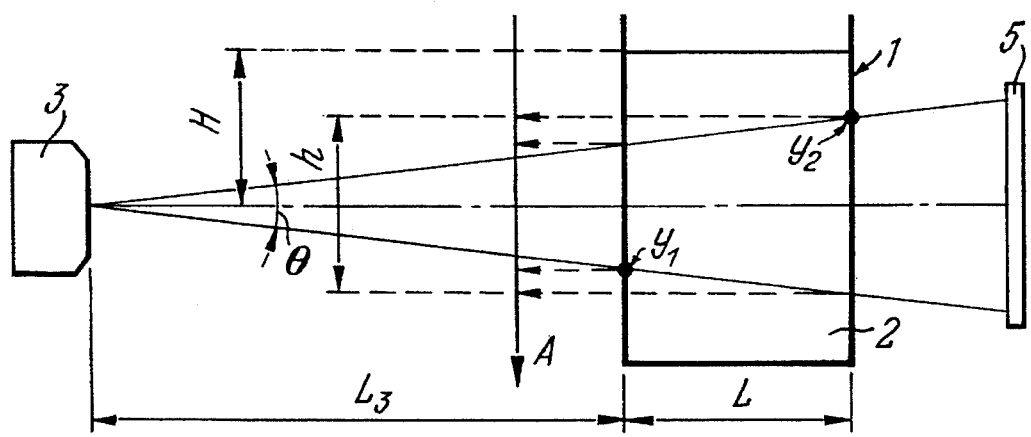
FIG. 8 is a schematic view of a cell and a beam of diverging rays, the axis of which is perpendicular to the direction of sedimentation, according to the present invention.

A converging beam 4 of rays (FIG. 7) can also be used, the axis of which is positioned at an incident angle β to the direction of sedimentation and the convergence angle Θ is determined from the condition $$L_1\sin\left(\beta+\frac{\gamma}{2}\right) - L_2\sin\left(\beta-\frac{\gamma}{2}\right) \leq 2.83 H\sigma^{1/2},$$

where $L_1$ is the maximum distance from the cone apex to the intersection of the beam of rays with the far wall of the cell, $L_2$ is the minimal distance from the cone apex to the intersection of the beam of rays with the near wall of the cell. An embodiment is also possible when a diverging beam 4 of rays (FIG. 8) is used, the axis of which is perpendicular to the direction of sedimentation and the divergence angle θ is determined from the condition $$2(L+L_3)tg\frac{\theta}{2} \leq 2.83 H\sigma^{1/2}.$$

The axis of the beam 4 of rays may be positioned at an incident angle β (FIG. 1) to the direction of sedimentation. Wherein the divergence angle θ is determined from the condition $$L_4\sin\left(\beta+\frac{\theta}{2}\right) - L_5\sin\left(\beta-\frac{\theta}{2}\right) \leq 2.83 H\sigma^{1/2}.$$

To implement the proposed method beams are used which are within the wavelength of from 0.6 μ to 0.05 μ.

The photoelectric method of sedimentation analysis of dispersion systems of a homogeneous substance is conducted in the following manner.

A suspension is prepared from the powder of a homogeneous substance, whose degree of dispersion is to be determined, and a dispersion medium which is taken to be a transparent liquid. The suspension is loaded into a measuring cell 1 (FIG. 1) with transparent walls. It is assumed that in the initial state the particles are uniformly dispersed throughout the whole volume of the suspension. In that state the concentration of the suspension is constant. It is also assumed that the particles descend at Stoke's velocity. For particles of radius this velocity is determined by the equation where $$\alpha = \frac{2(\rho_m - \rho_g)g}{9\eta}, \quad (2)$$

$\rho_m$ is the density of the powder particle material, $\rho_g$ is the density of the dispersion liquid, g is the acceleration of gravity, η is the viscosity of the liquid.

The descending suspension is used as a scatterer of the bean if rays falling on one of the cell walls. Preliminary, in the photoelectric method the intensity of the radiation passing through the unloaded cell 1 (FIG. 1) is measured. Then the same method is used to determine the dependence on time of the intensity of radiation of the beam of rays not scattered by the suspension. These data are used to determine the dependence on time of the optical density of the descending suspension that is irradiated by the beam of rays.

The optical density at the moment of time t is

D(t)=ln $I_o/I_t$ where $I_o$ is the measured value of the photocurrent which is a result of the radiation which has passed through the unloaded cell, $I_t$ is the value of the photocurrent which is a result of radiation non-scattered by the suspension at any moment of time t>0 after the beginning of sedimentation. The optical density changes in time only from the moment t=τ. By that time the largest particles, initially on the surface of the suspension will enter the region of the cell which is exposed to the radiation beam. The tank is to use the cited data to determine all the characteristics of the degree of dispersion due to the geometric conditions of interaction between the radiation and the suspension, taking into account the Brownian movement of the particles.

These characteristics are as follows. First of all, this is the density of particle distribution ν (r) in the powder sample in accordance with the values of their Stoke's radius. The product ν(r)dr is equal to the fraction of those particles whose size is in the infinitely small interval from r to (r+dr). Therefore, $$\int_0^{r_{max}} \nu(r)dr = 1. \tag{3}$$

In expression (3) $r_{max}$ designates the radius of the largest powder particles.

In the second place, the degree of dispersion is characterized by the density of powder mass distribution μ(r) according to the values of particle radii. It also makes it possible to determine the fraction of the mass present for any infinitely small interval of radius values. The value μ(r) is related to the density ν(r) by the relationship $$\mu(r) = \frac{r^3 \nu(r)}{\int_0^{r_{max}} r^3 \nu(r) dr} \tag{4}$$

and satisfies the condition, similar to (3)

$$\int_0^{r_{max}} \mu(r)dr = 1. \tag{5}$$

The densities of distribution ν(r) and μ(r) provide the maximum comprehensive and exhaustive characteristic of the degree of dispersion. These values allow the fraction of particles or mass of the powder to be determined which belong to any finite interval of radius $(r_1, r_2)$ values from 0 to $r_{max}$. These fractions are determined by the integrals $$\int_{r_1}^{r_2} \nu(r)dr \text{ and } \int_{r_1}^{r_2} \mu(r)dr.$$

If the mass M of a selected powder sample is known, then the quantities $$M\mu(r)dr \text{ and } M \int_{r_1}^{r_2} \mu(r)dr$$

are equal to the masses which belong respectively to an infinitely small interval (r, r+dr) and any finite interval $(r_1, r_2)$ of values of particle radii.

In addition to the mentioned integral distributions which are related to the density ν(r), the following integral characteristics of the degree of dispersion are necessary for a full analysis: the mean radius of the particles <r>

$$<r> = \int_0^{r_{max}} r\nu(r)dr, \tag{6}$$

the mean value of the squared radius <r²>

$$<r^2> = \int_0^{r_{max}} r\nu(r)dr, \tag{7}$$

and the mean standard deviation Δ

$$\Delta = (<r^2> - <r>^{2})^{1/2}/<r> \tag{8}$$

As a rule, when a beam of rays is used, a small-angle scattered radiation is added to the radiation being registered. This addition is negligibly small if φ/2π<<1, where φ is the maximum divergence angle at which the registering photocell is seen from the illuminated points on the side walls of the measuring cell (FIG. 1).

This condition is easily met if beams are used which are not too wide and have small angular divergence. In that case it is sufficient to position the registering photocell at a small distance from the measuring cell. This distance should be much greater than the size of the registering photocell. Thus, if the beam of rays is parallel and its axis is perpendicular to the direction of sedimentation, then a receiving photocell which is about b 5mm in size can be positioned at a distance of about 10 cm from the measuring cell.

In accordance with the known orientation of each ray in the beam, defined by a singular vector $\vec{n}$ along the ray, it is always possible to determine the orientation of the beam as a whole, giving it the mean value of $\vec{n}$. Let it be assumed that the length of beam propagation in this direction inside the cell equals L, i.e. the distance between the walls of the cell. Then $$\ln \frac{P(L,t)}{P_o} = -\pi n L \int_0^{r_{max}} dr r^2 \nu(r) p(r,t) \tag{9}$$

where P(L, t) is the power of the non-scattered part of the radiation emerging at a moment of time t from a cell loaded with the suspension, $P_o$ is the power of radiation that has passed through a cell with a pure dispersive liquid, n is the number of scattering centers in a unit of suspension volume at the beginning of sedimentations.

The quantity p(r,t) represents that part of the cell volume with the suspension after breakdown into layers, which at the moment of time t is in the beam zone and is positioned in the layer comprising particles of one radius $r_1$.

Since P(L, t)=I(t) and $P_o=I_o$, the optical density of the suspension is $$D(t) = \pi n L \int_o^{r_{max}} dr \cdot r^2 \nu(r) p(r,t). \tag{10}$$

The relationship (10) is the basis for obtaining all the subsequent results. The following properties of the function p(r,t) allow those results to be obtained. The shape of the beam of rays is selected.

The maximum length h of the projection of the line between the two furtherest spaced from each other points $y_1$ and $y_2$ of two light spots $X_1, X_2$, created by the non-scattered beam of rays on the walls of the unloaded cell, on the axis 6 parallel to the direction of sedimentation A, is determined for each shape of the beam of rays used.

Let it be assumed that the middle of that projection h at the initial moment of time t=0 is at a depth H relative to the surface of the suspension.

The general derivation of the basic equations, in accordance with which the aforesaid parameters characterizing the degree of dispersion of powder are determined, is provided below.

At first consideration will be given to the general case when the beam of rays is displaced at a constant scanning velocity U relative to a cell with a suspension in a direction parallel to the direction of sedimentation.

Figure 9:
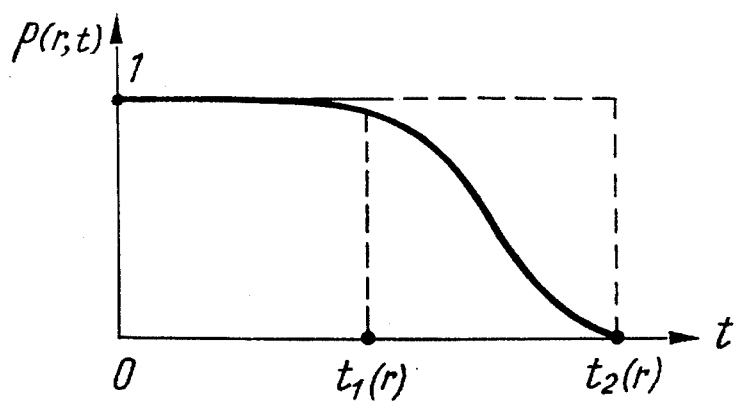
FIG. 9 is a diagram of changes in the quantity p(r,t) for a predetermined radius r of particles during a time t, according to the invention.

Let consideration be given to two moments of time $t_{1,2}(r)$ (FIG. 9) determined from the equation $$H \pm \frac{h}{2} = (U+v)t_{1,2}(r) = (U + \alpha r^2)t_{1,2}(r) \tag{11}$$

At the moment of time $t_1(r)$ particles of radius r begin to disappear from the system of scattering centers, and this disappearance is completed at the moment $t_2(r)$. Consequently, $$\frac{dp(r,t)}{dt} \neq 0$$

only for t in the interval

If the side surface of the beam intersects the walls of the cell along lines having a curvature other than zero at points $y_1$ and $y_2$ (FIG. 1), then $$\frac{dp(r,t)}{dt}$$

is continuous at points $t_{1,2}(r)$.

In accordance with the foregoing, $$\frac{dp(r,t)}{dt}$$

can be presented as $$\frac{dp(r,t)}{dt} = \begin{cases} \zeta(t) = H(t) - \alpha r^2 t, \ H(t) = H - Ut, \\ 0, \text{ with } t < t_1(r), \ t > t_2(r) \\ -q(r,t) \frac{1}{t_2(r) - t_1(r)} \left[ \frac{((h/2)^2 - \zeta_r^2(t))^{1/2}}{\frac{h}{2}} \right] \end{cases} \tag{12}$$

q(r,t) is a slowly changing function, the values of which are approximately unity. In (12) the quantity in the square brackets ensures smooth transition to zero of the derivative $$\frac{dp(r,t)}{dt}$$

at points $t_{1,2}(r)$. It can be obtained from (11) and (12) that $$\upsilon_D(t) = \frac{\pi n L}{h} \int \sqrt{\frac{H(t) + h/2}{\alpha t}} \sqrt{\frac{H(t) - h/2}{\alpha t}} dr \cdot q(r,t) r^2 (\alpha r^2 + u) \cdot$$

$$v(r) \frac{[(h/2)^2 - \zeta_r^2(t)]^{1/2}}{h/2}$$

Here $\upsilon_D(t)=dD/dt$ is the velocity of change of the optical density at a moment of time t. With H>>h/2 and the moment of time t, for which H(t)>>h/2 is also valid, the function q(r,t) in the right-hand part of the obtained equation can with a high degree of accuracy be regarded as being equal to unity.

A new integration variable X is now introduced by the relationship:

$$r = p(t)(1 + \Theta(t)X)^{1/2}$$

where $p(t) = [H(t)/\alpha(t)]^{1/2}$ and $\Theta(t) = h/2H(t)$.

The variable X changes within the limits of from −1 to +1. The following is obtained as a result thereof:

$$\frac{2h}{K\pi n L \gamma(t)} - \frac{1}{\alpha p^5(t)} \cdot \upsilon_D(t) = \int_{-1}^{+1} dx(1 + \gamma(t) \cdot X)^{1/2} \cdot$$

$$(1 + \gamma(t) \cdot X + \beta) \cdot (1 - X^2)^{1/2} \cdot v_p(t) (1 + \gamma(t) \cdot X)^{1/2}$$

where $\beta = U/\alpha p^2(t)$.

Since it is assumed that $\Theta(t) \ll 1$, the last integral is to a high degree of accuracy equal to the first terms of its expansion into a Taylor series to the powers $\Theta(t)$. Limiting the power to the second power and making the required integration, it is found that $$\frac{2h}{K\pi n L \gamma} - \frac{1}{\alpha p^5} \cdot \upsilon_D(t) =$$

$$\frac{\pi}{2} (1 + \beta)v(p) \left\{ 1 + \gamma^2 \left[ \frac{1}{8(1+\beta)} - \frac{1}{32} + \frac{1}{16} \frac{\rho dv}{v dp} + \right. \right.$$

$$\left. \left. \frac{1}{8(1+\beta)} \frac{p \, dv}{v \, dp} + \frac{1}{32 v} \frac{p^2 \, d^2 v}{dp^2} \right] \right\}$$

To make the notations shorter the argument t for the p, $\Theta$, $\beta$ quantities is omitted.

The processes of crushing, pulverizing, dispersing and the like, used in the production of powder materials, do not as a rule have differential selectivity. This means that the densities of distribution v (p), which have to be dealt with in practice, do not have sharp peaks. In such cases $$p/v \frac{dv}{dp} \cong 1$$

and accordingly $$p^2/v \frac{d^2v}{dp^2} \ll 1.$$

Consequently, the following assessment is valid for the quantities included in the square brackets in the last equation: its approximate value does not exceed 0.28 $\Theta^2$.

Let it be assumed that the margin of accuracy is 0.5 $\Theta^2$, which is the methodical accuracy. Then with $\Theta \ll 1$, $$v(r) = -A^{-1} \frac{H(t)}{r^3(\alpha r^2 + U)} . \tag{13}$$

In (13) p has been replaced by r and $$A = \frac{K\pi^2 n L}{8} = \text{const.} \tag{14}$$

This constant is determined by equation (3). According to (14) it immediately fixes the product of KnL.

The conducted analysis is based on relationship (9), where it is assumed that the volume of the suspension in the cell which is in the zone of the beam only depends on the radius of the particles, and this dependence is quadratic.

Actually, there is also a dependence on the shape of the particles, the state of their surface and a number of other factors. As a result there is strictly speaking only a direct proportional relationship between the volume of the suspension in the zone of the beam and the quantity $\pi r^2$. Wherewith the factor of proportionality will range from 2 to 10. This is taken into account in equation (14) by means of the quantity K. Equation (3) determines the effect of all of the aforementioned factors, relating them to the integral normative characteristic of the analysis as a whole.

The first case to be given consideration is that when the beam of rays is stationary with the condition that h<<H.

In that case U=O and H(t)=H, so that in accordance with (13) and with the methodical error $\Sigma=0.5(j/2H)^2$ $$v(r) = -B^{-1} |v_D(t)/\alpha r^5|_{t=H/\alpha r^2}$$

where $B^{-1}=A^{-1}H$ and in accordance with (3) is determined from the equation $$B = \int_0^{r_{max}} dr \frac{v_D(t)}{\alpha r^5} \Big|_{t=\frac{H}{\alpha r^2}} \quad (15)$$

A new variable $t=H/\alpha r^2$ is introduced into (15) instead of the variable of integration r. The time at which the optical density begins to drop is designated by $\tau$. This time is equal to $$\tau = H/\alpha r_{max}^2 \quad (16)$$

Equation (15) is now integrated by parts. As a result $$B = (r_{max}/2) \left\{ \tau^{3/2} D(\tau) + \tau^{1/2} \int_\tau^\infty dt D(t) \right\}$$

Thus, when the beam of rays is stationary $$v(r) = \frac{2}{r_{max}} \frac{(t^{5/2} v_D(t))|_{t=H/\alpha r^2}}{\tau^{3/2} D(\tau) + \tau^{1/2} \int_\tau^\infty dt D(t)} \quad (17)$$

In accordance with the definitions (4), (6) and (7), after making the necessary transformations, $$M(r) = \frac{2}{r_{max}} \frac{t \, v_D(t)|_{t=H/\alpha r^2}}{D(\tau) - \frac{\tau^{1/2}}{2} \int_\tau^\infty \frac{dt}{t^{3/2}} D(t)} \quad (18)$$

$$<r> = r_{max} \frac{1 + \left(\frac{1}{2\tau^{1/2} D(\tau)}\right) \int_\tau^\infty \frac{dt}{t^{1/2}}}{1 + \frac{1}{\tau D(\tau)} \int_\tau^\infty dt D(t)} \quad (19)$$

$$<r^2> = \frac{r_{max}^2}{1 + \frac{1}{\tau D(\tau)} \int_\tau^\infty dt(D(t))} \quad (20)$$

Consideration will now be given to a photoelectric method in which scanning of a beam of rays is effected in the course of conducting sedimentation analysis of dispersion systems, i.e. the beam of rays is displaced at a constant scanning velocity U upwards parallel to the direction of sedimentation.

This mode is possible if the source of radiation is arranged substantially lower with respect to the surface of the suspension, than is provided for by the methodical error defined by the equation $H=0.35 \, h/6\frac{1}{2}$.

This depth is designated as $(H+\Delta H)$, and then the scanning velocity will be $U=\Delta H/T$, where T is the scanning time.

The analysis may be conducted faster when $T>\tau$. Here $\tau$ is the time when the largest particles appear in the moving beam. This will take place when $H/\alpha r_{max}^2 < \Delta H/U$, i.e. if $$U < \alpha r_{max}^2 (\Delta H/H). \quad (21)$$

For example, on the basis of an analysis made with a coarse sieve it is possible to rapidly assess the approximate value of the radius $r_{max}$ and Stoke's velocity for the largest particles.

In order to get an impression of the possible values of velocity U and scanning time T, consideration will now be given to the aforementioned conditions of translucency in which with $\rho=0.1\%$, H equals 0.3 cm. Let $\Delta H=1.8$ cm and $r_{max} \approx 10 \, \mu = 10^{-5}$ m. With $\alpha=3.27\times10^6$ l/m·s using (21) then $U<2\times10^{-3}$ m/s=2 mm/s and $T \geq 10^2 s \approx 1.5$ min.

The practical expediency of establisying as initial excessive depth of exposure to radiation with subsequent use of a scanning mode is that these procedures are effective means for excluding the effect of transient processes in the suspension, that may occur when it is loaded in the measuring cell, on the results of analysis.

In the mode of scanning the density of particle distribution $v(r)$ is determined by expression (13) with $H(t)=H+\Delta H-Ut$ with $t \leq T$ and also by expression (13) but with $H(t)=H=$const. with $t \geq T$. Consequently, in that case the integration determining the constant A in (13) is modified. As a result of integration the following expression is obtained for $v(r)$:

$$v(r) = \frac{2}{r_{max}} \frac{[A_1(t) \cdot t^{5/2} \, v_D(t)]|_{t=\frac{H(t)}{\alpha r^2}}}{\tau^{3/2} D(t) + \tau^{1/2} \int_\tau^\infty dt B_1(t) D(t)} \quad (22)$$

The quantities $r_{max}$ and $\tau$ in (22) are related to each other by another relationship $$r_{max} = \sqrt{\frac{H + \Delta H - U\tau}{\alpha \tau}} \quad (23)$$

Functions $A_1(t)$ and $B_1(t)$ are determined by the equations $$A_1(t) = \quad (24)$$

-continued $$B_1(t) = \begin{cases} \dfrac{(H+\Delta H - U\tau)^{3/2}}{(H+H)(H+\Delta H - Ut)^{1/2}} & \text{with } \tau \leq t \leq T \\ \dfrac{(H+\Delta H - U\tau)^{3/2}}{(H+\Delta H - Ut)^{3/2}} & \text{with } t > T \end{cases} \quad (25)$$

$$\begin{cases} \dfrac{(H+\Delta H)(H+\Delta H - U\tau)}{(H+\Delta H - Ut)^2} & \text{with } \tau \leq t \leq T \\ \dfrac{H+\Delta H - U\tau}{H+\Delta H - Ut} & \text{with } t > T \end{cases}$$

After corresponding conversions are made the following expression is obtained for the distribution density $\mu(r)$ $$M(r) = \quad (26)$$

$$-\dfrac{2}{r_{max}} \dfrac{A_2(t) \cdot r_{UD}(t)|_t = \dfrac{H(t)}{\alpha r^2}}{D(\tau) + C(\tau,T) \cdot D(T) - \dfrac{\tau^{1/2}}{2} \int_\tau^\infty \dfrac{dt}{t^{3/2}} B_2(t) D(t)}$$

The quantity $H(t)$ in (26) is determined in the same way as was used to determine $v(r)$, while $r_{max}$ and $\tau$ are related by the equation (23). The functions $A_2(t)$, $C(96, T)$ and $B_2(t)$ are defined by the equations $$A_2(t) = \begin{cases} \dfrac{(H+\Delta H - Ut)}{(H+\Delta H)} & \text{with } \tau \leq t \leq T \\ 1 & \text{with } t > T \end{cases} \quad (27)$$

$$C(\tau,T) = \left(\dfrac{\tau}{T}\right)^{1/2} \dfrac{(H+\Delta H - UT)^2}{(H+\Delta H - U\tau)^2} - \dfrac{(H+\Delta H - UT)^{1/2}}{(H+\Delta H - U\tau)^{1/2}} \quad (28)(29)$$

$$B_2(t) = \begin{cases} \dfrac{H+\Delta H}{(H+\Delta H - Ut)^{1/2}(H+\Delta H - U\tau)^{1/2}} & \text{with } t \leq T \\ \dfrac{(H+\Delta H - UT)^{1/2}}{(H+\Delta H - U\tau)^{1/2}} & \text{with } t > T \end{cases}$$

Finally, the following expressions are obtained for the quantities $\langle r_n \rangle$, $\langle r^2 \rangle$ $$r = r_{max} \dfrac{1 + \dfrac{1}{2\tau^{1/2} D(\tau)} \int_\tau^\infty \dfrac{dt}{t^{1/2}} B_3(t) D(t)}{1 + \dfrac{1}{\tau D(\tau)} \int_\tau^\infty dt B_1(t) D(t)} \quad (30)$$

where $B_1$ is as defined above, $$B_3(t) = \begin{cases} \dfrac{H+\Delta H}{H+\Delta H - Ut} & \text{with } t \leq T \\ \dfrac{(H+\Delta H - U\tau)^{1/2}}{(H+\Delta H - UT)^{1/2}} & \text{with } t \geq T \end{cases} \quad (31)$$

Then $$\langle r^2 \rangle = \dfrac{r_{max}^2}{1 + \dfrac{1}{\tau D(\tau)} \int_\tau^\infty dt B_1(t) D(t)} \quad (32)$$

It is evident from a comparison of the equations for characterizing the degree of dispersion related to the stationary beam of rays and to the scanning mode, that when the scanning velocity tends to zero (U→O), equations (22) and (26) go to (17) and (18) respectively.

It is known that when the amount of small-size particles having radii in the range from 5 to 0.01 μ is being measured under conditions of natural sedimentation, the effect of gravitational forces is very weak while the effect of thermal motion is substantial.

The effect of Brownian motion of particles on the results of analysis will now be assessed, taking a given error into account. Without taking that motion into account the border of spatial distribution of the particles of any radius, which is closer to the free surface of the suspension, will remain planar as it descends. The Brownian motion smears this plane into a strip, the width of which at the moment of time t is approximately equal to $l_r=(D_r \cdot t)^{1/2}$, where the diffusion coefficient $D_r$ of the particles of radius r is equal to $$D_r = kT/6\pi r \eta, \quad (33)$$

where k is Boltzmann's constant, T is the absolute temperature of the suspension.

The effect of the smearing is insignificant if $l \ll h$.

If $r_{min}$ is the radius of the smallest particles of powder, the time of photosedimentation analysis of the degree of dispersion of the particles is equal to:

$$T_1 = H/\alpha r_{min}^2.$$

Therefore, it should be that $(D_{r_{min}} \cdot T_1)^{1/2} \ll h$.

The following inequality is derived from (2), (33) and the expression for methodical error $\sigma$ $$\dfrac{0.12}{\sigma} \dfrac{K}{(\rho_m - \rho_g)g \, r_{min}^3} \dfrac{T}{H} \ll 1 \quad (35)$$

If this quantity is $\ll 1$, then the Brownian motion of the particles can be neglected.

Let it be assumed that the condition (35) is satisfied for a suspension having a temperature T, the interaction of which with a beam of radiation is characterized by certain values of $\sigma$ and H, and consequently of h. The methodical error of the results $\sigma=0.5 \, (h/2H)^2$ makes it possible to analyze how rational the conditions are under which the method is carried out.

It is evident that the relationship (35) will not change while $\sigma$=constant, if both T and H are simultaneously increased the same number of times. Consequently, the possibility to raise the temperature of the suspension does exist, but this will not affect the results of photosedimentation analysis of the degree of dispersion. This is important because the viscosity of the liquid phase of the suspension $\eta$ is not included in (35), and when the temperature rises it drops in accordance with an exponential law $\eta \sim \exp W/KT$, where W is the energy of activation of a viscous flow. It follows from (2) and (34) that $T_1$ is identical to $H\eta$. Therefore, the analyzing time is reduced if H and T are identically increased. Furthermore, when the temperature of the suspension is increased, coagulation of the suspension particles does not take place.

EXAMPLE 1

Consideration is given to porcelain powder with $\rho_m=2.5\times 10^3$ kg/m³. Let $r_{min}=0.1$ $\mu=10^{-7}$ m, the powder is dispersed in water with $\rho_g=10^3$ kg/m³ at room temperature T=293° K.

The obtained suspension interacts with a beam of rays under the following conditions: H=0.3 cm=0.3×10⁻² m, h=0.03 cm=0.3×10⁻³ m. Then $\sigma=0.5(h/2H)^2=0.001$ or 0.1%. Inserting these values and K=1.38×10⁻²³ into the left part of (35) the numerical value thereof is determined $$\frac{0.12 \cdot 1.38 \times 10^{-23} \, J/k \cdot 293° \, K.}{10^{-3} \cdot 1.5 \times 10^3 \, kg/m^3 \, 9.8 \, m/s^2 \cdot 10^{-21} \, m^3 \cdot 0.3 \, 10^{-2} \, m} = 0.1$$

Therefore, the condition (35) is fulfilled, if the temperature is raised approximately 1.136 times to 333° K. (60° C.) and H and h are increased the same number of times to respectively 0.34 cm and 0.034 cm. Taking into account that the viscosity of water at a temperature of 333° K. (60° C.) is 2.19 times less than the viscosity at room temperature, then in accordance with (2) and (34), after heating the suspension to 60° C. the analyzing time is reduced almost two times. The viscosity of water at room temperature is $\eta=10^{-3}$ kg/m·s. With this value of $\eta$ the coefficient $\alpha$ from (2) is $\alpha=3.27\times10^6$ 1/m·s. It follows from equation (34) that the full analyzing time at room temperature is $T_1=0.91\times10^5$ s which is equal to 25 hours. At a temperature of 333° K. (60° C.) it is approximately 12.5 hours.

The effectiveness of the established dependence of the methodical error on the quantities h and H will now be shown.

For example, let it be assumed that a beam of X-rays is used, the radius of the cross section of which is R=2h=2.5×10⁻³ cm. The depth at which the beam passes through the suspension is approximately 10 cm. Theoretically, with such a beam it is possible to conduct an analysis with a methodical error $\delta=0.5\%$, irradiating the suspension at a mere depth of H=10R=2.5×10⁻² cm. However, the choice of such a depth is not rational in view of the rapid exit of large particles from the system and the obvious influence of perturbations in the suspension, caused by its introduction into the measuring cell, on that stage of sedimentation. If H is selected to be H=0.5 cm, which is 20 times more than the earlier mentioned depth of 10 cm, and, accordingly, the measuring time is reduced 20 times (for example, from 18 hours to 0.9 hours for a sample having a density $\rho=3.17$ in water at 32° C.), then all the characteristics on the degree of dispersion can be obtained with a methodical error $$\sigma = 0.5 \left( \frac{2.5 \times 10^{-3}}{0.25} \right)^2 = 1.25 \times 10^{-5} \, (\cong 0.001\%)$$

All the possibilities for reducing the photosedimentation analyzing time, following from the claimed invention, will now be listed.

In the stationary mode this is achieved by selection of the irradiation depth H, which is minimal from the point of view that the required methodical accuracy of measurement is ensured at a predetermined shape of the beam of rays. The analyzing time is also substantially reduced in the scanning mode when thin beams of rays are used and highly dispersed particles are measured. The temperature of the suspension can also be raised, meeting the condition (35). The last possibility consists in that it is not the characteristics of differential dispersion themselves that are determined, but the ratios of their various values showing how many times particles having one radius or resultant mass thereof are greater or less than the particles of another radius, or correspondingly, resultant mass. These ratios, determined, for example in the stationary mode by equations $$\frac{v(r_1)}{v(r_2)} = \frac{t^{5/2} v_D(t)|_t = \frac{H}{\alpha r_1^2}}{t^{5/2} v_D(t)|_t = \frac{H}{\alpha r_2^2}}$$

$$\frac{m(r_1)}{m(r_2)} = \frac{t v_D(t)|_t = \frac{H}{\alpha r_1^2}}{t v_D(t)|_t = \frac{H}{\alpha r_2^2}}$$

do not comprise the values of optical density in all moments of measuring time.

EXAMPLE 2

An example is provided below on the realization of the proposed method of sedimentation analysis of the degree of dispersion of "Centriforce abrasive" quartz sand of high purity (FIGS. 3 and 4).

The following data are fed into a microprocessor:

the density $\rho_m=2.65\times10^{-3}$ kg per cu. m;

the methodical analysis error $\sigma$, for example, no more than 0.15% over the whole range of particle size;

the measurement temperature T=20° C.;

a beam of rays of cylindrical shape from a helium-neon laser source is used with R=6.5×10⁻⁴ m, the axis of which is perpendicular to the direction of sedimentation, wherein the depth H at which the axis of the beam is positioned relative to the surface of the suspension, is set at H=1.22×10⁻² m; the value of H is fed into the microprocessor; and the value h=2R=13×10⁻⁴ m is also fed into the computer;

distilled water is used as the dispersion liquid, this determining the value of Stoke's factor $\alpha$, for example, $\alpha=35\times10^5$ m⁻¹¹ s⁻¹.

The beam of rays is passed through the unloaded cell and the initial value of the photocurrent $I_o$ is determined, for example, $I_0=207$ mA. In this example, suspension irradiation is carried out at a constant depth H without scanning.

The necessary volume of the suspension, prepared by mixing quartz sand and water, is fed into the measuring cell using a dosing device, for example, syringe. After that the microprocessor turns on the current time sensor and the calculation program. The period of time $\tau$ is measured during which the optical density of the suspension remains constant from the moment sedimentation begins. In this example $\tau=3$ sec. In accordance with Stoke's equation taking this period of time $\tau$ into account, the radius of the largest powder particles $$r_{max} = \sqrt{\frac{H}{\alpha \tau}}$$

is determined, for example, with $\tau=3$ sec., $r_{max}=34$ μ.

The following measurements are made in the process of sedimentation after predetermined periods of time, for example, 0.1; 1; 10; 30 sec;

The value of the photocurrent I(t) created by the non-scattered part of the beam passing through the cell (see the table below), the values of the radii of particles descending in the suspension $$r(t') = \sqrt{\frac{H}{\alpha \tau}}.$$

The corresponding values of the relative optical density $D(t) = \ln I_o/I_t$ and the velocity at which it changes $$v_D(t) = \frac{dD(t)}{dt}$$

with $t > \tau$ are determined.

On the basis of the determined values of these parameters the density $v(r)$ of powder particle distribution and the density of powder mass distribution $\mu(R)$ according to particle radii are determined using equations (17) and (18). Furthermore, without direct determination of those distribution functions the integral characteristics of the degree of dispersion of powder particles corresponding thereto are found:

the mean value of the radius $\langle r \rangle$ of dispersed particles, the mean square value $\langle r^2 \rangle$ and the standard deviation $\Delta$ using equations (19), (20).

In this example randomly selected values of t, I, r are presented in the table, after which the calculated values of $\langle r \rangle$, $\langle r^2 \rangle$, $\Delta$, $\bar{r} = \sqrt{\langle r^2 \rangle}$ are presented.

TABLE

| t, sec | $I_m$ mA | r, M |
|---|---|---|
| 3 | 104.0 | 34.0 |
| 50 | 107.0 | 8.35 |
| 100 | 111.0 | 5.90 |
| 150 | 122.0 | 4.82 |
| 200 | 135.0 | 4.17 |
| 250 | 145.0 | 3.73 |
| 300 | 153.0 | 3.40 |
| 350 | 162.0 | 3.15 |
| 400 | 175.0 | 2.95 |
| 450 | 179.0 | 2.78 |
| 500 | 183.0 | 2.64 |
| 550 | 187.0 | 2.51 |
| 600 | 188.0 | 2.41 |
| 650 | 190.0 | 2.31 |
| 700 | 193.0 | 2.23 |
| 750 | 194.0 | 2.15 |
| 800 | 197.0 | 2.08 |
| $\langle r \rangle$ = 3.39M, | $\langle r^2 \rangle$ = 11.93M$^2$, | |
| $\bar{r}$ = 3.45M, | $\Delta$ = 0.2. | |

The measuring time, including the analyzing time in the stationary mode with the predetermined value of relative methodical error for the particular powder, is approximately 20 minutes.

EXAMPLE 3

When measurements are made using the scanning mode, the steps indicated in the stationary mode in example 2 should be carried out.

In this case:

The beam of rays is so arranged that the middle of the line h is at a depth $(H+\Delta H)$ from the surface of the suspension, where H is determined according to the value of the predetermined methodical error $\sigma$; $H=0.35 (h/\sigma)^{1/2}$, and the depth $(H+\Delta H)$ should be less than the distance from the surface of the suspension to the bottom of the cell, for example, $\Delta H=1$ cm;

the velocity of scanning is calculated under the condition that $$U < \alpha r_{max}^2 \frac{\Delta H}{H}, \; U \leq 3.3 \times 10^{-1} \text{ cm/sec},$$

where $r_{max}$, for example, is determined in the stationary mode, the scanning time $T_f = \Delta H/U = 3$ sec is determined, examples of calculations of $\Delta H$, U, T are presented on page 35;

after loading the cell with the suspension, displacement of the source of radiation 3 and photocell 5 is carried out in the direction opposite to the direction of sedimentation at a constant velocity $U \leq 3.3 \times 10^{-1}$ cm/sec;

The period of time $\tau$ is measured during which the optical density of the suspension D(t) remains constant from the moment scanning begins.

The subsequent steps are similar to the stationary mode, and the calculation of $v(r)$, $\mu(r)$ and the integral characteristics of the degree of dispersion of the powder particles is carried out according to corresponding equations (22), (26), and (30), (32) for the scanning mode. Wherein some functions of time $A_1(t)$, $B_1(t)$, $C(\tau_1, T)$, $A_2(t)$, $B_2(t)$ and $B_3(t)$ are calculated using the presented expressions with $H(t)=H+\Delta H-Ut$ and $\tau \leq t \leq T$.

The measuring time, including the analyzing time in the scanning mode with a predetermined value of methodical error for each powder and the used beam of rays, was substantially less than 20 minutes.

EXAMPLE 4

An example is now provided showing how the proposed method of sedimentation analysis of the degree of dispersion (FIG. 1) is effected using the stationary mode (example 2) and the scanning mode (example 3).

In this case:

a diverging beam of rays is used emitted from a source of radiation 3 which has an annular cross section, the axis of which is directed at an angle $\beta$ to the direction of sedimentation A, the angle being 15°;

a helium-neon laser is used as the source 3;

the angle of beam divergence is $\theta = 10^{-3}$ rad.

In view of the fact that $\theta \ll \beta$ and $$L_4 \sin (\beta+\theta/2) - L_5 \sin (\beta-\theta/2) \leq .83 \; H5^{1/2}$$

where $L_4$ is the maximum distance from the source 3 to the intersection of the beam of rays with the far wall of the cell at point $y_2$:

$L_5$ is the minimum distance from the source 3 to the intersection of the beam of rays with the near wall of the cell at point $y_1$, these distances $L_4$, $L_5$ may have any value when the method is implemented.

The predetermined methodical error of analysis $\sigma$ is 0.15%.

The measurement temperature T=20° C.

The length h is determined, that length being the projection of a line between the two furtherest spaced from each other points $y_1$ and $y_2$ on axis 6 parallel to the axis of sedimentation A, of two light spots, which are created by the non-scattered beam of rays on the walls of an unloaded cell, the value of h being $h=1.3\times10^{-2}$ m.

The value of $H=0.35h/\sigma^{1/2}$ is determined by positioning the beam of rays so that the middle of the line h is at a depth (H+ΔH) from the surface of the suspension, this distance being less than the distance from the surface of the suspension to the bottom of the cell.

Distilled water with $\alpha=35\times10^5$ $m^{-1}s^{-1}$ was used as the dispersion liquid.

The beam of rays was passed through an unloaded cell and the value of the photocurrent $T_o$ created by the non-scattered beam was determined $-I_o=207$ mA;

a suspension prepared by mixing quartz sand and water was introduced into the measuring cell using a dosing device;

the period of time $\tau_2$, during which the optical density of the suspension of dispersed powder particles remained constant from the moment at which sedimentation began, was measured;

the relative optical density of the suspension $D(t)=\ln I_o/I_t$ was measured;

the maximum a radius of the largest particles which settle on the bottom of the cell during the time $\tau_2$ was calculated in a real scale of time $$r_{max} = \sqrt{\frac{H+\Delta H}{\alpha \tau_2}}.$$

Displacement of the beam of rays 4 and the photocell 5 was effected in the direction opposite to the direction of sedimentation at a constant velocity U $$U < \alpha r_{max}^2 \frac{\Delta H}{H},$$

the scanning time $T=\Delta H/U$ was determined;

displacement of the beam of rays was terminated when it reached the depth H.

If the process of sedimentation was not completed at the moment scanning was terminated, then measurement was continued in the stationary mode (example 2) until the value $I(t) \leq I_o$ was reached, after which the measurement process was terminated.

The density $v(r)$ of powder particle distribution is determined on the basis of the established values and the density of $\mu(r)$ of powder mass distribution is determined on the basis of the particle radii values obtained according to equation (22) and (26) for current time values when the stationary mode is used.

Wherein, some functions of time: $A_1(t)$, $B_1(t)$, $C(\tau_2, t)$, $A_2(t)$ and $B_2(t)$ are calculated for the values H(t)=H=const with $t \geq T$. Then calculations are made for current time values when the scanning mode is used (see, example 3).

Furthermore, without the direct determination of these distribution functions, the corresponding thereto integral characteristics of the degree of dispersion of powder particles are determined: the mean value of the radius <r> of the dispersed particles, the mean value of the squared radius $<r^2>$, and the standard deviation Δ using equations (30), (22).

Wherewith, some functions of time: $B_1(t)$ and $B_3(t)$ used to determine <r> or $<r^2>$ are calculated for the scanning mode with H(t)=H+ΔH−Ut with $\tau \leq t \leq T$, and for the stationary mode with H(t)=H=const with $t \geq T$.

The analyzing time was less than 20 minutes when two measurement modes were used with a predetermined value of measurement accuracy for a given powder and the beam of rays used.

EXAMPLE 5

In carrying out measurements with the use of discrete scanning, a beam of rays is disposed such that the middle of section h be at a depth of (H+ΔH) from the suspension surface, in this case (H+ΔH)<$H_{max}$.

After charging the vessel with a suspension of powder particles uniformly dispersed in a liquid, a step-by-step displacement of the beam is performed in a direction opposite to the direction of sedimentation with a step equal to h/2 during time ($t_1+t_2$), where $t_1$ is the time required to move the beam of rays by a step, and $t_2$ is the time required for measurement. The beam is moved at a speed of, for example, 10 mm/s, 5 mm/s, 2 mm/s, 1 mm/s, 0.5 mm/s, 0.2 mm/s. Time $t_2$ is calculated such that during this time authentic information is obtained about the coordinates of the beam with respect to the vessel and about the optical density of the suspension. For example, the conversion frequency of the analogue signals of a photosensor as a function of the required authenticity is effected with discreteness of 7 measurements in 0.1 s, 1 s, 10 s and in 1 min.

Then, time interval τ is measured during which the optical density of the suspension remains constant from the time instant sedimentation begins. In this case, for instance, the beam is displaced at a speed of 10 mm/s, and the conversion frequency of photocurrent I(t) is effected with a discreteness of not less than 7 measurements in 0.1 s. The authenticity of measurements equals 0.9999.

Radius $r_{max}$ of the coarsest particles of the powder is determined from Stoke's formula taking into account time interval τ

$$r_{max} = \sqrt{\frac{H+\Delta H - n(\tau) \cdot h/2}{\alpha \tau}}$$

wherein n (τ) is the number of steps taken up to time instant τ.

Then, the corresponding values of relative density and the rate of variation of the relative optical density are determined during each stop of the beam of rays for time $t_2$.

The following quantities are determined by the found values:

the density of distribution of the powder particles by their radii from the formula $$v(r) = \frac{2}{r_{max}} \frac{t^{5/2} V_D(t) \Big|_{t=\frac{H+\Delta H - n(t) \cdot h/2}{\alpha \cdot r^2}}}{\tau^{3/2} D(\tau) + \tau^{1/2} \int_\tau^\infty dt\, D'(t)}$$

wherein D'(t) is the averaged value of the relative optical density of the dispersion system in time $t_i$ between two adjacent stops of the beam and D'(t)=D(t) during time $t_2$, n is the number of steps with t>τ, the density of distribution of the powder mass by the particles radii from the formula $$\mu(r) = \frac{2}{r_{max}} \frac{t \cdot V_D(t) \Big|_{t=\frac{H+\Delta H - n(t) \cdot h/2}{\alpha r^2}}}{D(\tau) - \frac{\tau^{1/2}}{2} \int_\tau^\infty \frac{dt}{t^{3/2}} D'(t)}$$

The integral characteristics of powder dispersity are determined in a similar way.

average value of radius r $$<r> = r_{max} \frac{1 + \frac{1}{2} \tau^{1/2} D(\tau) \int_\tau^\infty \frac{dt}{t^{1/2}} D'(t)}{1 + \frac{1}{\tau D(\tau)} \int_\tau^\infty dt\, D'(t)}$$

average value of the radius squared $<r^2>$ of powder particles $$<r^2> = \frac{r_{max}^2}{1 + \frac{1}{\tau D(\tau)} \int_\tau^\infty dt\, D'(t)} - \text{standard deviation}$$

$$\Delta = \frac{(<r^2> - <r>^2)^{1/2}}{<r>}$$

Scanning is ceased when the beam reaches depth H.

If the sedimentation process is not completed to the time instant the scanning is ceased, measurement is continued under stationary conditions according to Example 2 to the value of $I(t) \leq I_0$ after which the measurement process is stopped.

Industrial Use

The claimed photoelectric method of sedimentation analysis of dispersion systems of a homogeneous substance may be used in practice in pharmacology, in the food industry for the production of starch, flour, dried milk, chocolate, coffee, etc., in the production of mineral fertilizers, and substances for protecting plants, in the production of synthetic materials, metallic powders, in powder metallurgy, in the production of building materials, e.g. cement, ceramics, quartz, glass, clay, etc., in the paint industry.

This method substantially reduces the time necessary for analysis of the degree of dispersion of powders used in technological processes which makes it possible to enhance the quality of the produced products and reduce power consumption.

We claim:

1. A photoelectric method of sedimentation analysis of dispersion systems of a homogeneous substance, wherein a ray is passed through an unloaded cell and the initial value of photocurrent, created by the non-scattered ray that has passed through the unloaded cell, is measured, the cell is loaded with a suspension of powder particles uniformly dispersed in a liquid, the value of the photocurrent created by the non-scattered part of the ray that has passed through the cell is measured in the process of sedimentation, the optical density D(t) of the suspension of dispersed powder particles is calculated using the equation $$D(t) = \ln I_o/I_t,$$

where $I_o$ is the value of the photocurrent created by the non-scattered ray that has passed through the unloaded cell, $I_t$ is the value of photocurrent created by the non-scattered part of the ray that has passed through the cell at a current moment t and, using Stoke's equation $$v = \alpha r^2,$$

the radii r of the particles that are descending in the suspension are determined, where v is the velocity of sedimentation of the particles and α is a proportionality coefficient determined by the equation $$\alpha = \frac{2(\rho_m - \rho_g)g}{g\eta}$$

where $\rho_m$ is the density of the powder particles, $\rho_g$ is the density of the liquid phase at the measurement temperature, g is the acceleration of gravity, η is the dynamic viscosity of the liquid phase at the measurement temperature, characterized in that, a beam of rays from a radiation source is used, the beam having an arbitrary cross-sectional shape, and the projection length h of the line between two furtherest spaced from each other points of two light spots, which are created by the non-scattered beam of rays on the two opposite walls of an unloaded cell, where h extends along an axis parallel to the direction of sedimentation, is determined for each beam shape of source rays used, the value of the relative methodical error σ is preset using the equation $$\sigma = .5(h/2H)^2$$

to a value within the range of from 0.1% to 0.00001%, this being used to determine the value of H, using the equation $$H = .35 h \sigma^{1/2},$$

the beam of rays is disposed so that the middle of the line h is at a depth H from the surface of the suspension, the time interval τ during which the optical density of the suspension of dispersed particles remains constant from the moment sedimentation begins is measured, and the relative optical density of the suspension D(τ) during that time interval τ is measured using the equation $$D(\tau) = \ln I_o/I_t,$$

the maximum radius $r_{max}$ of the largest particles of the powder is determined taking this time interval τ into account and using Stoke's equation, by $$r_{max} = \sqrt{\frac{H}{\alpha \tau}},$$

the velocity $v_D$ at which the relative optical density changes with t>τ is determined, using the equation $$v_D = \frac{dD(t)}{dt},$$

and the density $v(r)$ of powder particle distribution is determined as a function of the radius, using the equation $$v(r) = -\frac{2}{r_{max}} \frac{t^{5/2} v_p(t) | t = H/\alpha r^2}{t^{3/2} D(\tau) + \tau^{1/2} \int_\tau^\infty dt D(t)}$$

2. A photoelectric method as claimed in claim 1, characterized in that scanning of the beam of rays is effected when sedimentation analysis of dispersion systems is being carried out, and accordingly the beam of rays is positioned so that the middle of line h is at a depth of $(H+\Delta H)$ from the surface of the suspension, wherein $$(H+\Delta H) < H_{max},$$

where $H_{max}$ is the distance from the surface of the suspension to the bottom of the cell, after the cell is loaded with a suspension of uniformly dispersed powder particles, the beam of rays is displaced in a direction opposite to the direction of sedimentation at a constant velocity U determined by the inequality $$U < \alpha r_{max}^2 \frac{\Delta H}{H},$$

the time interval $\tau_1$ during which the optical density of the suspension of dispersed particles remains constant from the moment the scanning begins is measured, the radius of the largest powder particles is determined using Stoke's equation and taking the time interval $\tau_1$ into account $$r_{max} = \sqrt{\frac{H+\Delta H - U\tau_1}{\alpha \tau_1}},$$

the scanning time $T = \Delta H/U$ is determined, the density $v(r)$ of the powder particle distribution as a function of radius is determined using the equation $$v(r) = \frac{2}{r_{max}} - \frac{A_1(t) t^{5/2} \cdot v_D(t) | t = H(t)/\alpha r^2}{\tau_1^{3/2} D(\tau_1) + \tau_1^{1/2} \int_{\tau_1}^\infty dt (B_1(t) D(t))}$$

where $$A_1(t) = \begin{cases} \frac{(H+\Delta H - U\tau_1)^{3/2}}{(H+\Delta H)(H+\Delta H - Ut)^{1/2}} & \text{with } \tau_1 \le t \le T \\ \frac{(H+\Delta H - U\tau_1)^{3/2}}{(H+\Delta H - UT)^{3/2}} & \text{with } t > T \end{cases}$$

-continued $$B_1(t) = \begin{cases} \frac{(H+\Delta H)(H+\Delta H - U\tau_1)}{(H+\Delta H - Ut)^2} & \text{with } \tau_1 \le t \le T \\ \frac{H+\Delta H - U\tau_1}{H+\Delta H - UT} & \text{with } t > T \end{cases}$$

and the scanning is terminated when the beam reaches the depth H.

3. A photoelectric method as claimed in claim 1, characterized in that scanning of the beam of rays is effected when sedimentation analysis of dispersion systems is being carried out, and accordingly the beam of rays is so positioned that the middle of line h is at a depth $(H+\Delta H)$ from the surface of the suspension, wherein $$(H+\Delta H) < H_{max},$$

where $H_{max}$ is the distance from the surface of the suspension to the cell bottom, after the cell is loaded with a suspension of uniformly dispersed powder particles, the time interval $\tau_2$ during which the optical density of the suspension of dispensed powder particles remains constant from the moment sedimentation begins is measured prior to the scanning, taking this time interval $\tau_2$ into account, the radius $r_{max}$ of the largest particles of powder is determined using Stoke's equation, in accordance with equation $$r_{max} = \sqrt{\frac{H+\Delta H}{\alpha \tau_2}}$$

from the moment $\tau_2$ the beam of rays is displaced in the direction opposite to the direction of sedimentation at a constant velocity U, determined by the inequality $$U < \alpha r_{max}^2 \frac{\Delta H}{H},$$

the scanning time $T = \Delta H/H$ is determined, and the density $v(r)$ of the powder particle distribution as a function of radius is determined using the equation $$v(r) = \frac{2}{r_{max}} - \frac{A_1(t) t^{5/2} v_D(t) | t = H(t)/\alpha r^2}{\tau_2 D(\tau_2) + \tau_2^{1/2} \int_{\tau_2}^\infty dt (B_1(t) D(t))}$$

where $$A_1(t) = \begin{cases} \frac{(H+\Delta H - U\tau_2)^{3/2}}{(H+\Delta H)(H+\Delta H - Ut)^{1/2}} & \text{with } \tau_2 \le t \le T \\ \frac{(H+\Delta H - U\tau_2)^{3/2}}{(H+\Delta H - UT)^{3/2}} & \text{with } t > T \end{cases}$$

-continued $$B_1(t) = \begin{cases} \dfrac{(H+\Delta H)(H+\Delta H - U\tau_2)}{(H+\Delta H - Ut)^2} & \text{with } \tau_2 \leq t \leq T \\ \dfrac{H+\Delta H - U\tau_2}{H+\Delta H - UT} & \text{with } t > T \end{cases}$$

and the scanning is terminated when the beam reaches the depth H.

4. A photoelectric method of sedimentation analysis of dispersion systems of a homogeneous substance, wherein
- a ray is passed through as unloaded cell and the initial value of the photocurrent created by the non-scattered ray that has passed through the unloaded cell is measured,
- the cell is loaded with a suspension of uniformly dispersed powder particles,
- the value of the photocurrent created by the non-scattered part of the ray that has passed through the cell is measured in the process of sedimentation,
- the relative optical density D(t) of the suspension of dispersed powder particles is measured using the equation $$D(t) = \ln I_o/I_t,$$

where $I_o$ is the value of the photocurrent created by the non-scattered ray that has passed through the unloaded cell, $I_t$ is the value of the photocurrent created by the non-scattered part of the ray that has passed through the cell at a current moment of time t and, using Stoke's equation $$\upsilon = \alpha r^2,$$

the values of the radii r of the particles that are descending in the suspension are determined, where $\upsilon$ is the velocity of particle sedimentation and $\alpha$ is a proportionality coefficient determined by the equation $$\alpha = \dfrac{2(\rho_m - \rho_g)g}{g\eta}.$$

where $\rho_m$ is the powder particle density, $\rho_g$ is the density of the liquid phase of the suspension, $\eta$ is the dynamic viscosity of the liquid phase at the measurement temperature, and g is the acceleration of gravity, characterized in that
- a beam of rays from a radiation source is used, the beam having an arbitrary cross-sectional shape,
- the projection length h of the line between two furtherest spaced from each points of two light spots, which are created by the non-scattered beam of rays on the two opposite walls of the unloaded cell, where h extends along an axis parallel to the direction of sedimentation, is determined for each beam shape of source rays used,
- the value of the relative methodical error $\sigma$ is preset using the equation $$\sigma = .5(h/2H)^2$$

to a value within the range of from 0.1% to 0.00001%, this being used to determine the value of H, using the equation $$H = .35h\sigma^{1/2}$$

the beam of rays is disposed so that the middle of the line h is at a depth H from the surface of the suspension,
the time interval $\tau$ during which the optical density of the suspension of dispersed powder particles remains constant from the moment when sedimentation begins is measured, and the relative optical density $D(\tau)$ during that time interval $\tau$ is measured using the equation $$D(\tau) = \ln I_o/I_t,$$

the radius $r_{max}$ of the largest powder particles is determined taking this time interval into account and using Stoke's equation, $$r_{max} = \sqrt{\dfrac{H}{\alpha\tau}},$$

the velocity of changes in the relative optical density $\upsilon_D$ with $t > \tau$ is determined using the equation $$\upsilon_D = \dfrac{dD(t)}{dt},$$

and the density $\mu(r)$ of the powder mass distribution is determined according to the values of radii of the powder particles, using the equation $$\nu(r) = \dfrac{2}{r_{max}} - \dfrac{t\upsilon_D(t)|t = H/\alpha r^2}{D(\tau) - \dfrac{1}{2}\tau^{1/2}\displaystyle\int_\tau^\infty \dfrac{dt}{t^{3/2}} D(t)}$$

5. A photoelectric method as claimed in claim 4, characterized in that scanning of the beam of rays is effected when sedimentation analysis of dispersion systems is being carried out, accordingly,
the beam of rays is positioned so that the middle of the line h is at a depth of (H+ΔH) from the surface of the suspension, wherein $$(H+\Delta H) < H_{max},$$

where $H_{max}$ is the distance from the surface of the suspension to the bottom of the cell,
after the cell is loaded with a suspension of uniformly dispersed powder particles the beam is displaced in a direction opposite to the direction of sedimentation at a constant velocity U which is determined by the inequality $$U < \alpha r_{max}^2 \dfrac{\Delta H}{H},$$

the time interval $\tau_1$ during which the optical density of the suspension of dispersed powder particles remains constant from the moment scanning begins is measured,
the radius of the largest powder particles is determined, using Stoke's equation and taking the time interval $\tau_1$ into account, by $$r_{max} = \sqrt{\frac{H + \Delta H - U\tau_1}{\alpha \tau_1}},$$

the scanning time $T = \Delta H/U$ is determined, and the density $\mu(r)$ of the distribution of the powder mass as a function of radius is determined using the equation $$v(r) = \frac{2}{r_{max}} - \frac{A_2(t) v_D(t) | t = H(t)/\alpha r^2}{D(\tau_1) + C(\tau_1,T)D(T) - \frac{1}{2}\tau_1^{1/2} \int_{\tau_1}^{\infty} \frac{dt}{t^{3/2}} B_2(t)D(t)}$$

where $$A_2(t) = \begin{cases} \frac{H + \Delta H - Ut}{H + \Delta H} & \text{with } \tau_1 \leq t \leq T \\ 1 & \text{with } t > T \end{cases}$$

$$C(\tau_1,T) = \left(\frac{\tau_1}{T}\right)^{1/2} \left[\frac{(H + \Delta H - UT)^2}{(H + \Delta H - U\tau_1)^2} - \frac{(H + \Delta H - UT)^{1/2}}{(H + \Delta H - U\tau_1)^{1/2}}\right]$$

$$B_2(t) = \begin{cases} \dfrac{H + \Delta H}{(H + \Delta H - Ut)^{1/2}(H + \Delta H - \Delta\tau_1)^{1/2}} & \text{with } t \leq T \\ \dfrac{(H + \Delta H - UT)^{1/2}}{(H + \Delta H - U\tau_1)^{1/2}} & \text{with } t \geq T \end{cases}$$

$$M(r) = \frac{2}{r_{max}} - \frac{A_2(t) v_p(t)| t = H(t)/\alpha r^2}{D(\tau_2) + C(\tau_2,T)D(T) - \frac{\tau_2^{1/2}}{2} \int_{\tau_2}^{\infty} \frac{dt}{t^{3/2}} B_2(t)D(t)}$$

where $$A_2(t) = \begin{cases} \frac{H + \Delta H - Ut}{H + \Delta H} & \text{with } \tau_2 \leq t \leq T \\ 1 & \text{with } t > T \end{cases}$$

$$C(\tau_2,T) = \left(\frac{\tau_2}{T}\right)^{1/2} \left[\frac{(H + \Delta H + UT)^2}{(H + \Delta H - U\tau_2)^2} - \frac{(H + \Delta H - UT)^{1/2}}{(H + \Delta H - U\tau_2)^{1/2}}\right]$$

and the scanning is terminated when the beam reaches the depth H.

6. A photoelectric method as claimed in claim 4, characterized in that scanning of the beam of rays is effected when sedimentation analysis of dispersion systems is being conducted, accordingly the beam of rays is so positioned that the middle of the line is at a depth $(H+\Delta H)$ from the surface of the suspension, wherein $$(H+\Delta H) < H_{max},$$

where $H_{max}$ is the distance from the surface of the suspension to the bottom of the cell, after the cell is loaded with a suspension of powder particles uniformly dispersed in a liquid, the interval of time $\tau_2$ during which the optical density of the suspension of dispersed powder particles remains constant from the moment sedimentation begins is measured prior to the scanning, the radius $r_{max}$ of the largest powder particles is determined using Stoke's equation and taking time interval $\tau_2$ into account, using the equation $$r_{max} = \sqrt{\frac{H + \Delta H}{\alpha \tau_2}},$$

displacement of the beam of rays is conducted from the moment of time $\tau_2$ in a direction opposite to the direction of sedimentation at a constant velocity U, as determined by the inequality $$U < \alpha r_{max}^2 \frac{\Delta H}{H},$$

the scanning time $$T = \Delta H/U$$

is determined, and the density $\mu(r)$ of the distribution of powder mass is determined according to the values of the radii of powder particles $$B_2(t) = \begin{cases} \dfrac{H + \Delta H}{(H + \Delta H - Ut)^{1/2}(H + \Delta H - U\tau_2)^{1/2}} & \text{with } t \leq T \\ \dfrac{(H + \Delta H - UT)^{1/2}}{(H + \Delta H - U\tau_2)^{1/2}} & \text{with } t \geq T \end{cases}$$

and the scanning is terminated when the beam reaches the depth H.

7. A photoelectric method of sedimentation analysis of dispersion systems of a homogeneous substance, wherein a ray is passed through an unloaded cell and the initial value of the photocurrent created by the non-scattered ray that has passed through the unloaded cell is measured, the cell is loaded with a suspension of powder particles uniformly dispersed in a liquid, the photocurrent which is created by the non-scattered part of the ray that has passed through the cell is measured during sedimentation, the relative optical density D(t) of the suspension of dispersed powder particles is measured, using the equation $$D(t) = \ln I_o/I_t,$$

where $I_o$ is the value of the photocurrent created by the non-scattered ray that has passed through the unloaded cell, $I_t$ is the value of the photocurrent created by the non-scattered part of the ray that has passed through the cell at a current moment of time t, and using Stoke's equation $$\upsilon = \alpha r^2,$$

the value of the radii r of the particles that are descending in the suspension are determined, where $\upsilon$ is the velocity of particle sedimentation and $\alpha$ is a proportionality coefficient, determined by the equation $$\alpha = \frac{2(\rho_m - \rho_g)g}{g\eta}.$$

where $\rho_m$ is the powder particle density, $\rho_g$ is the density of the liquid phase of the suspension, $\eta$ is the dynamic viscosity of the liquid phase at the measurement temperature, g is the acceleration of gravity, characterized in that a beam of rays from a source of radiation is used, the beam having an arbitrary cross-sectional shape, the projection length h of the line between the two furtherest spaced from each other points of two light spots, which are created by the non-scattered beam of rays on the two opposite walls of the unloaded cell, where h extends along on the axis parallel to the direction of sedimentation, is determined for each beam shape of source rays used, the value of relative methodical error $\sigma$ is preset using the equation $$\sigma = .5 \, (h/2H)^2$$

to within the range of from 0.1% to 0.0001%, this being used to determine the value of H, using the equation $$H = .35h\sigma^{1/2},$$

the beam of rays is disposed so that the middle of the line h is at a depth H from the surface of the suspension, the interval of time $\tau$ during which the optical density of the suspension of dispersed powder particles remains constant from the moment at which sedimentation begins is measured, and the relative optical density of the suspension $D(\tau)$ in that time interval is measured according to the equation $$D(\tau) = \ln I_o/I_t,$$

using Stoke's equation and taking into account that interval of time $\tau$ the radius of the largest particles of powder is determined by the equation $$r_{max} = \sqrt{\frac{H}{\alpha\tau}},$$

the velocity of change of the relative optical density $\upsilon_D$ with $t > \tau$ is determined using the equation $$\upsilon_D = \frac{dD(t)}{dt},$$

and the integral characteristics of the degree of dispersion of the powder particles are determined: the mean value of the radius $<r>$ of powder particles by the equation $$<r> = r_{max} \frac{1 + \frac{1}{2\tau^{1/2} D(t)} \int_\tau^\infty \frac{dt}{t^{1/2}} D(t)}{1 + \frac{1}{\tau D(\tau)} \int_\tau^\infty dt D(t)}$$

the mean square value of the radius $<r^2>$ of the powder particles by the equation $$<r^2> = \frac{r_{max}^2}{1 + \frac{1}{\tau D(\tau)} \int_\tau^\infty dt D(t)}$$

and the standard deviation $\Delta$ between the radius and the squared radius by the equation $$\Delta = \frac{(<r^2> - <r>^2)^{1/2}}{<r>}.$$

8. A photoelectric method as claimed in claim 7, characterized in that scanning of the beam of rays is effected when sedimentation analysis of dispersion systems is being carried out, accordingly the beam of rays is positioned so that the middle of the line h is at a depth (H+$\Delta$H) from the surface of the suspension, wherein $$(H+\Delta H) < H_{max}$$

where $H_{max}$ is the distance from the surface of the suspension to the bottom of the cell, after the cell is loaded with a suspension of uniformly dispersed powder particles, the beam is displaced in a direction opposite to the direction of sedimentation at a constant velocity U which is determined by the inequality $$U < \alpha r_{max}^2 \frac{\Delta H}{H},$$

the time interval $\tau_1$ during which the optical density of the suspension of dispersed powder particles remains constant from the moment the scanning begins is measured, the radius of the largest powder particles is determined using Stoke's equation and taking time interval $\tau_1$ into account $$r_{max} = \sqrt{\frac{H + \Delta H - U\tau_1}{\alpha \tau_1}},$$

the scanning time $T = \Delta H/U$ is determined, and the integral characteristics of the degree of dispersion of the powder particles are determined: the mean value of the radius $<r>$ of powder particles by the equation $$<r> = r_{max} \frac{1 + \frac{1}{2\tau_1^{1/2} D(\tau_1)} \int_{\tau_1}^{\infty} \frac{dt}{t^{1/2}} B_3(t) D(t)}{1 + \frac{1}{\tau_1 D(\tau_1)} \int_{\tau_1}^{\infty} dt B_1(t) D(t)}$$

where $B_1$ is as defined above, $$B_3(t) = \begin{cases} \dfrac{H + \Delta H}{H + \Delta H - Ut} & \text{with } t \leq T \\[6pt] \dfrac{(H + \Delta H - U\tau_1)^{1/2}}{(H + \Delta H - UT)^{1/2}} & \text{with } t \geq T \end{cases}$$

the mean square value of the radius of the powder particles $<r^2>$ by the equation $$<r^2> = \frac{r_{max}^2}{1 + \frac{1}{\tau_1 D(\tau_1)} \int_{\tau_1}^{\infty} dt B_1(t) D(t)}$$

and the standard deviation $\Delta$ between the radius and the squared radius $$\Delta = \frac{(<r^2> - <r>^2)^{1/2}}{<r>}$$

and the scanning is terminated when the beam reaches the depth H.

9. A photoelectric method as claimed in claim 7, characterized in that scanning of the beam of rays is effected when sedimentation analysis of dispersion systems is being carried out, accordingly the beam of rays is so positioned that the middle of the line is at a depth $(H + \Delta H)$ from the surface of the suspension, wherein $$(H + \Delta H) < H_{max}$$

where $H_{max}$ is the distance from the surface of the suspension to the bottom of the cell, after the cell is loaded with a suspension of powder particles uniformly dispersed in a liquid, the interval of time $\tau_2$ during which the optical density of the suspension of dispersed powder particles remains constant from the moment sedimentation begins is measured prior to the scanning, the radius $r_{max}$ of the largest powder particles is determined according to Stoke's equation, taking that interval of time $\tau_2$ into account, in accordance with equation $$r_{max} = \sqrt{\frac{H + \Delta H}{\alpha \tau_2}},$$

the beam of rays is displaced from the moment of time $\tau_2$ in a direction opposite to the direction of sedimentation at a constant velocity U, determined by the inequality $$U < \alpha r_{max}^2 \frac{\Delta H}{H},$$

the scanning time $T = \Delta H/U$ is determined and the integral characteristics of the degree of dispersion of the powder particles are determined: the mean value of the radius $<r>$ of powder particles by the equation $$<r> = r_{max} \frac{1 + \frac{1}{2\tau_2^{1/2} D(\tau_2)} \int_{\tau_2}^{\infty} \frac{dt}{t^{1/2}} B_3(t) D(t)}{1 + \frac{1}{\tau_2 D(\tau_2)} \int_{\tau_2}^{\infty} dt B_1(t) D(t)}$$

where $B_1$ is as defined above, $$B_3(t) = \begin{cases} \dfrac{H + \Delta H}{H + \Delta H - Ut} & \text{with } t \leq T \\[6pt] \dfrac{(H + \Delta H - U\tau_2)^{1/2}}{(H + \Delta H - UT)^{1/2}} & \text{with } t \geq T \end{cases}$$

the means square value of the radius $<r^2>$ of the powder particles by the equation $$<r^2> = \frac{r_{max}^2}{1 + \frac{1}{\tau_2 D(\tau_2)} \int_{\infty}^{\tau_2} dt B_1(t) D(t)}$$

and the standard deviation $\Delta$ between the radius and the squared radius $$\Delta = \frac{(<r^2> - <r>^2)^{1/2}}{<r>}$$

and the scanning is terminated when the beam reaches the depth H.

10. A photoelectric method as claimed in claim 1 characterized in that the suspension of powder particles uniformly dispersed in a liquid is heated to a temperature of $T°K$. at which the Brownian motion of the smallest powder particles having a radius of from 5 μ to 0.01 μM can be neglected, and the distance H from the surface of the suspension to the middle of the line h is increased proportionally so that the condition $$\frac{0.12 \cdot K}{G(\rho_m - \rho_g) g \, r_{min}^3} - \frac{T}{K} \ll 1$$

where k is Boltzmann's constant, is maintained.

11. A photoelectric method as claimed in claim 1, characterized in that a beam of rays of cylindrical shape with a radius R of the cross section is used, the axis of which is perpendicular to the direction of sedimentation and is positioned at the depth H.

12. A photoelectric method as claimed in claim 1, characterized in that a beam of rays of cylindrical shape with a radius R of the cross section is used, the axis of which is positioned at an incident angle $\beta$ to the direction of sedimentation and is determined from the condition $$L \, tg \, \beta + \frac{2R}{\cos\beta} \leq 2.83 \, H\sigma^{1/2}$$

where L is the distance between the two opposite walls of the cell.

13. A photoelectric method as claimed in claim 1, characterized in that a converging beam of rays is used, the axis of which is perpendicular to the direction of sedimentation and the convergence angle $\gamma$ is determined from the condition $$2(L + L_o) \, tg \, \frac{\gamma}{2} \leq 2.83 \, H\sigma^{1/2}$$

where $L_o$ is the distance from the cone apex to the near wall along a normal thereto, and where L is the distance between the two opposite walls of the cell.

14. A photoelectric method as claimed in claim 1 characterized in that a converging beam of rays is used, the axis of which is positioned at an incident angle $\beta$ to the direction of sedimentation, and the convergence angle $\gamma$ of which is determined from the condition $$L_1 \sin\left(\beta + \frac{\gamma}{2}\right) - L_2 \sin\left(\beta - \frac{\gamma}{2}\right) \leq 2.83 \, H\sigma^{1/2}$$

where $L_1$ is the maximum distance from the cone apex to the intersection of the beam of rays with the far wall of the cell, $L_2$ is the minimum distance from the cone apex to the intersection of the beam of rays with the near wall of, the cell.

15. A photoelectric method as claimed in claim 1, characterized in that a diverging beam of rays is used, the axis of which is perpendicular to the direction of sedimentation, and the divergence angle $\theta$ is determined from the condition $$2(L + L_3) \, tg \, \frac{\theta}{2} \leq 2.83 \, H\sigma^{1/2}$$

where $L_3$ is the distance from the source of radiation to the near wall of the cell along a normal thereto, and where L is the distance between the two opposite walls of the cell.

16. A photoelectric method as claimed in claim 1, characterized in that a diverging beam of rays is used, the axis of which is positioned at an incident angle $\beta$ to the direction of sedimentation, and the divergence angle $\theta$ is determined from the condition $$L_4 \sin\left(\beta + \frac{\theta}{2}\right) - L_5 \sin\left(\beta - \frac{\theta}{2}\right) \leq 2.83 \, HG^{1/2}$$

where $L_4$ is the maximum distance from the source to the intersection of the beam of rays with the far wall of the cell, and where $L_5$ is the minimum distance from the source to the intersection of the beam with the near wall of the cell.

17. A photoelectric method as claimed in claim 1, characterized in that rays are used which are within the wavelength band of from 0.6 μ to 0.05 μ.

18. A photoelectric method as claimed in claim 1, characterized in that in conducting the sedimentation analysis of dispersion systems, discrete scanning by a beam of rays is performed for which purpose the beam is disposed such that the middle of section h be at a depth of (H+ΔH) from the suspension surface, in which case (H+ +ΔH)<$H_{max}$, wherein $H_{max}$ is the distance from the suspension surface to the bottom of the vessel, after charging the vessel with a suspension of powder particles uniformly dispersed in a liquid, a step-by-step displacement of the beam is performed in a direction opposite to the direction of sedimentation with a step equal to h/2 during time ($t_1+t_2$), where $t_1$ is the time required to move the beam of rays by a step, and where L is the distance between the two opposite walls of the cell and $t_2$ is the time required for measurement after the beam is stopped, radius $r_{max}$ of the coarsest powder particles is determined from Stoke's formula taking into account time interval $\tau$ $$r_{max} = \sqrt{\frac{H + \Delta H - n(\tau) h/2}{\alpha \tau}}$$

wherein $n(\tau)$ is the number of steps taken up to time instant $\tau$, during each stop of the beam, the rate of variation of the relative optical density $V_D$ and the relative optical density $D(t)$ during the time of measurement $t_2$ are determined at t>$\tau$, the values of the density of distribution of the powder particles $v(r)$, by their radii r from the formula $$v(r) = \frac{2}{r_{max}} \frac{t^{5/2} V_D(t) \Big|_{t = \frac{H + \Delta H - n \cdot h/2}{\alpha r^2}}}{\tau^{3/2} D(\tau) + \tau^{1/2} \int_\tau^\infty dt \, D'(t)}$$

where D'(t) is the averaged value of the relative optical density of the dispersion system in time $t_1$ between two adjacent stops of the beam and D'(t)=D(t) during time $t_2$, and n is the number of steps with t>$\tau$, scanning is ceased when the beam reaches depth H.

19. A photoelectric method as claimed in claim 4, characterized in that in conducting the sedimentation analysis of dispersion systems, discrete scanning by a beam of rays is performed for which purpose the beam is disposed such that the middle of section h be at a depth of (H+ΔH) from the suspension surface, in which case $(H+\Delta H) \leq H_{max}$, wherein $H_{max}$ is the distance from the suspension surface to the borrom of the vessel, after charging the vessel with a suspension of powder particles uniformly dispersed in a liquid, a step-by-step displacement of the beam is performed in a direction opposite to the direction of sedimentation with a step equal to h/2 during time $(t_1+t_2)$, where $t_1$ is the time required to move the beam of rays by a step, after which a stop of the beam occurs, and $t_2$ is the time required for measurement after the beam is stopped, radius $r_{max}$ of the coarsest powder particles is determined from Stoke's formula taking into account time interval τ

$$r_{max} = \sqrt{\frac{H + \Delta H - n(\tau) h/2}{\alpha r^2}}$$

wherein n(τ) is the number of steps taken up to time instant τ, during each stop of the beam, the rate of variation of the relative optical density $V_D$ and the relative optical density D(t) during the time of measurement $t_2$ are determined at t>τ, the values of the density of distribution of the powder mass μ(r) by the radii r from the formula $$\mu(r) = \frac{2}{r_{max}} \cdot \frac{t \cdot V_D(t) \big|_{t = \frac{H + \Delta H - n \cdot h/2}{\alpha r^2}}}{D(\tau) - \frac{\tau^{1/2}}{2} \int_\tau^\infty \frac{dt}{t^{3/2}} D'(t)}$$

where D'(t) is the averaged value of the relative optical density of the dispersion system in time $t_1$ between two adjacent stops of the beam and D'(t)=D(t) during time $t_2$, n is the number of steps with t>τ, scanning is stopped when the beam reaches depth H.

20. A photoelectric method as claimed in claim 7, characterized in that in conducting the sedimentation analysis of dispersion systems, discrete scanning by a beam of rays is performed for which purpose the beam is disposed such that the middle of section h be at a depth of (H+ΔH) from the suspension surface, in this case $(H+\Delta H) \leq H_{max}$, wherein $H_{max}$ is the distance from the suspension surface to the bottom of the vessel, after charging the vessel with a suspension of powder particles uniformly dispersed in a liquid, a step-by-step displacement of the beam is performed in a direction opposite to the direction of sedimentation with a step equal to h/2 during time $(t_1+t_2)$, where $t_1$ is the time required to move the beam of rays by a step, after which a stop of the beam occurs and $t_2$ is the time required for measurement after the beam is stopped, radius $r_{max}$ of the coarsest powder particles is determined from Stoke's formula taking into account time interval τ

$$r_{max} = \sqrt{\frac{H + \Delta H - n(\tau) h/2}{\alpha r^2}}$$

wherein n(τ) is the number of steps taken up to time instant τ, during each stop of the beam, variations of the relative optical density D(t) during the time of measurement $t_2$ are determined at t>τ, the integral characteristics of dispersity of the powder particles are determined:

average value of radius <r>

$$<r> = r_{max} \left[ 1 + \frac{\left(\frac{1}{2} \tau^{1/2} D(\tau) \int_\tau^\infty \frac{dt}{t^{1/2}} D'(t)\right)}{1 + \frac{1}{\tau D(\tau)} \int_\tau^\infty dt\, D'(t)} \right]$$

wherein D'(t) is the averaged value of the relative optical density of the dispersion system in time $t_1$ between two adjacent stops of the beam end D'(t)=D(t) during time $t_2$, average value of the radius squared $<r^2>$ of powder particles $$<r^2> = \frac{r_{max}^2}{1 + \frac{1}{\tau D(\tau)} \int_\tau^\infty dt\, D'(t)}$$

standard deviation Δ

$$\Delta = \frac{(<r^2> - <r>^2)^{1/2}}{<r>}$$

scanning is ceased after the beam reaches depth H.

* * * * *